US009812263B2

(12) United States Patent
Hanaya et al.

(10) Patent No.: US 9,812,263 B2
(45) **Date of Patent: *Nov. 7, 2017**

(54) COMPOUND AND PHOTOELECTRIC CONVERSION DEVICE

(71) Applicant: ADEKA CORPORATION, Tokyo (JP)

(72) Inventors: Minoru Hanaya, Gunma (JP); Kenji Kakiage, Gunma (JP); Masafumi Unno, Gunma (JP); Yohei Aoyama, Tokyo (JP); Toru Yano, Tokyo (JP); Daisuke Sawamoto, Tokyo (JP); Hiroyuki Osada, Tokyo (JP)

(73) Assignee: ADEKA CORPORATION, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/081,023

(22) Filed: Mar. 25, 2016

(65) Prior Publication Data

US 2016/0211085 A1 Jul. 21, 2016

Related U.S. Application Data

(62) Division of application No. 14/003,452, filed as application No. PCT/JP2012/055755 on Mar. 7, 2012.

(30) Foreign Application Priority Data

Apr. 5, 2011 (JP) ................................ 2011-083421

(51) Int. Cl.

| | |
|---|---|
| ***H01L 31/04*** | (2014.01) |
| ***H01G 9/20*** | (2006.01) |
| ***H01L 51/00*** | (2006.01) |
| ***C07F 17/02*** | (2006.01) |
| ***C07F 7/18*** | (2006.01) |
| ***H01L 31/0256*** | (2006.01) |
| ***C09B 1/16*** | (2006.01) |
| ***C09B 23/01*** | (2006.01) |
| ***C09B 23/14*** | (2006.01) |
| ***C09B 23/16*** | (2006.01) |
| ***C09B 29/08*** | (2006.01) |
| ***C09B 57/00*** | (2006.01) |

(52) U.S. Cl.

CPC ........... *H01G 9/2059* (2013.01); *C07F 7/184* (2013.01); *C07F 7/1836* (2013.01); *C07F 7/1852* (2013.01); *C07F 17/02* (2013.01); *C09B 1/16* (2013.01); *C09B 23/0075* (2013.01); *C09B 23/14* (2013.01); *C09B 23/145* (2013.01); *C09B 23/164* (2013.01); *C09B 29/0808* (2013.01); *C09B 57/00* (2013.01); *H01G 9/2031* (2013.01); *H01L 31/0256* (2013.01); *H01L 51/006* (2013.01); *H01L 51/0068* (2013.01); *H01L 51/0072* (2013.01); *H01L 51/0073* (2013.01); *H01L 51/0083* (2013.01); *H01L 51/0094* (2013.01); *H01L 51/005* (2013.01); *H01L 51/007* (2013.01); *H01L 51/0052* (2013.01); *H01L 51/0055* (2013.01); *H01L 51/0061* (2013.01); *H01L 51/0065* (2013.01); *H01L 51/0071* (2013.01); *Y02E 10/542* (2013.01)

(58) Field of Classification Search

CPC ........ C07F 7/18; H01L 31/04; H01L 31/0256; H01M 14/00; H01G 9/2059

USPC ................. 252/519.31, 519.3, 500; 534/726; 136/263, 261; 546/14

See application file for complete search history.

(56) References Cited

U.S. PATENT DOCUMENTS

| | | | | |
|---|---|---|---|---|
| 9,530,571 | B2 * | 12/2016 | Aoyama | C09B 69/008 |
| 2009/0005557 | A1 | 1/2009 | Nakagawa et al. | |
| 2012/0012821 | A1 | 1/2012 | Langer | |

(Continued)

FOREIGN PATENT DOCUMENTS

| | | | | |
|---|---|---|---|---|
| EP | 2386607 | A2 * | 11/2011 | C09B 57/008 |
| EP | 2836607 | | 11/2011 | |

(Continued)

OTHER PUBLICATIONS

CAS Reg. No. 1402216-23-2, Oct. 29, 2012.*

(Continued)

*Primary Examiner* — Douglas M C Ginty

(74) *Attorney, Agent, or Firm* — Young & Thompson

(57) ABSTRACT

Disclosed is a novel compound represented by formula (1) below. In the formula, A represents an optionally substituted aromatic hydrocarbon ring or aromatic heterocyclic group, B represents a group including a chain of one to four pieces of one or more groups selected from groups represented by specific formulae (B-1) to (B-13) (such as —C≡C— or —N═N—, specifically see the description), R1 to R3 each represent an optionally substituted hydrocarbon or hydrocarbonoxy group, at least one of R1 to R3 represents an optionally substituted hydrocarbonoxy group, R4 and R5 each represent an optionally substituted hydrocarbon group, R4 and R5 may be linked together to form a ring, and R4 and R5 may be each independently linked with A to form a ring (1)

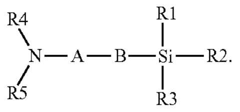

4 Claims, 1 Drawing Sheet

(56) References Cited

U.S. PATENT DOCUMENTS

| | | | | |
|---|---|---|---|---|
| 2014/0261647 | A1 | 9/2014 | Aoyama | |
| 2014/0299191 | A1 | 10/2014 | Akimoto | |
| 2015/0133603 | A1* | 5/2015 | Kramer | C07F 7/1836 524/590 |

FOREIGN PATENT DOCUMENTS

| | | |
|---|---|---|
| JP | 2008-063390 | 3/2008 |
| JP | 2009-269987 | 11/2009 |
| JP | 2010-027749 | 2/2010 |
| JP | 2011-026412 | 2/2011 |
| KR | 2010-0066158 | 6/2010 |
| WO | 02/01667 | 1/2002 |
| WO | 2006/120939 | 11/2006 |
| WO | 2008/056567 | 5/2008 |
| WO | 20100067996 | 6/2010 |

OTHER PUBLICATIONS

Kenji Kakiage, Masaki Yamamura, Masashi Unno, Toru Kyomen, Minoru Hanaya,"Applicability of Alkoxysilyl Groups as Anchor Moiety of Sensitizing Dye for Dye-sensitized Solar Cell" 89th Annual Meeting of the Chemical Society of Japan in Spring Koen Yokoshu I, Mar. 13, 2009 (Mar. 13, 2009), p. 481, 2 L2-16.

Kenji Kakiage, Masaki Yamamura, Masashi Unno, Toru Kyomen, Minoru Hanaya, "Alkoxysilyl Azobenzene-rui no Shikiso Zokan Taiyo Denchi ni Okeru Zokan Shikiso to shite no Kento", 2009 Nen Symposium on Photochemistry, Sep. 16, 2009 (Sep. 16, 2009), p. 142, 1P068.

Kenji Kakiage, Masaki Yamamura, Masashi Unno, Toru Kyomen, Minoru Hanaya, "Silyl Chikan Azobenzene-rui no Shikiso Zokan Taiyo Denchi ni Okeru Zokan Tokusei", 2010 Nen Symposium on Photochemistry, Sep. 8, 2010 ( Sep. 8, 2010), p. 155, 1P085.

International Search Report—PCT/JP2012/055755—dated Apr. 17, 2012.

Baik, Chul, et al. "Organic dyes with a novel anchoring group for dye-sensitized solar cell applications", Journal of Photochemistry and Photobiology A: Chemistry 201 (2009) 168-174.

Choi, Hyunbong, et al. "Synthesis of Novel Organic Dyes Containing Coumarin Moiety for Solar Cell," Bull. Korean Chem. Soc. 2007, vol. 28, No. 11, pp. 1973-1979.

* cited by examiner

COMPOUND AND PHOTOELECTRIC CONVERSION DEVICE

TECHNICAL FIELD

The invention relates to novel compounds, support materials produced with the novel compounds, and photoelectric conversion devices produced with the support materials.

BACKGROUND ART

Dyes have been widely used in a variety of technical fields. As an example in the field of photoelectric conversion devices such as solar cells, photosensitizing dyes are used in dye-sensitized photoelectric conversion devices. Such dye-sensitized photoelectric conversion devices are theoretically expected to have high efficiency and thought to be producible at a cost lower than that of traditional photoelectric conversion devices made with silicon semiconductors.

A dye-sensitized photoelectric conversion device has an electrode including an oxide semiconductor as a support on which a dye is supported. In such a dye-sensitized photoelectric conversion device, the dye is excited by absorbing incident light, and the excited dye injects electrons into the support to cause photoelectric conversion.

Techniques that have been studied to improve the conversion efficiency and durability of dye-sensitized photoelectric conversion devices include improvements in the dye-supporting ability of a support. Specifically, if physical or chemical adsorption ability of a dye to a support is increased, excited energy can be transferred with high efficiency from the dye to the support, and the dye can be prevented from leaching into the device (specifically, leaching into the electrolytic solution or the like). A technique of adding an anchor group such as a carboxylic acid group or a silanol group to dye molecules has been tried to improve the supporting ability (see Patent Literatures 1 to 3).

Solar cells are one of the important applications of dye-sensitized photoelectric conversion devices. Such solar cells are required to have high durability because of the nature of the intended use, but known dyes and photoelectric conversion devices made with such dyes still have insufficient performance.

CITATION LIST

Patent Literature

Patent Literature 1: Japanese Patent Application Laid-Open (JP-A) No. 2008-063390
Patent Literature 2: JP-A No. 2010-027749
Patent Literature 3: JP-A No. 2011-026412

SUMMARY OF THE INVENTION

Technical Problem

It is therefore an object of the invention to provide a dye having a high ability to adsorb to a support, to provide a support material carrying such a dye, and to provide a photoelectric conversion device with high efficiency and high durability.

Solution to Problem

As a result of earnest study, the inventors have found novel compounds having a specific structure and have completed the invention based on the finding that the object can be achieved with such novel compounds.

Specifically, the invention provides a novel compound represented by formula (1) below.

(1)

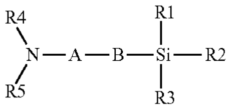

wherein

A represents an optionally substituted aromatic hydrocarbon ring group or an optionally substituted aromatic heterocyclic group, B represents a group comprising a chain of one to four pieces of one or more groups selected from groups represented by formulae (B-1) to (B-13) below, R1, R2, and R3 each represent an optionally substituted hydrocarbon group or an optionally substituted hydrocarbonoxy group, at least one of R1, R2, and R3 represents an optionally substituted hydrocarbonoxy group, R4 and R5 each represent an optionally substituted hydrocarbon group, R4 and R5 may be linked together to form a ring, and R4 and R5 may be each independently linked with A to form a ring, (B-1)

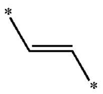

(B-2)

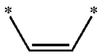

(B-3)

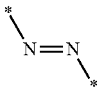

(B-4)

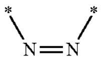

(B-5)

(B-6)

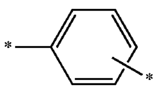

(B-7)

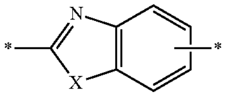

(B-8)

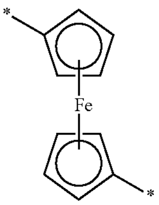

-continued (B-9)

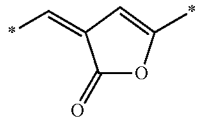

(B-10)

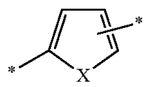

(B-11)

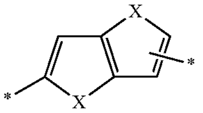

(B-12)

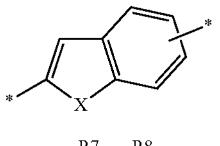

(B-13)

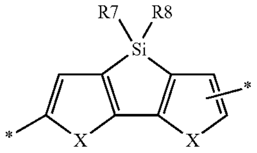

wherein

X represents S, O, or NR, wherein R represents an optionally substituted hydrocarbon group, and any hydrogen atom may be replaced by a fluorine atom, a chlorine atom, a bromine atom, an iodine atom, a cyano group, a nitro group, a hydroxyl group, a thiol group, an —NR7R8 group, or an optionally substituted aliphatic hydrocarbon group, wherein R7 and R8 each represent an optionally substituted hydrocarbon group.

The invention also provides a support material including a support and the novel compound of formula (1) supported on the support.

The invention also provides a photoelectric conversion device including an electrode having such a support material.

Effect of the Invention

The novel compound of the invention, which has an alkoxysilyl group, has a high ability to adsorb to a support. The compound and the photoelectric conversion device having the compound-carrying support material have high efficiency and high durability and are suitable for use in applications needed to have high durability, such as solar cells.

DESCRIPTION OF EMBODIMENTS

Figure 1:
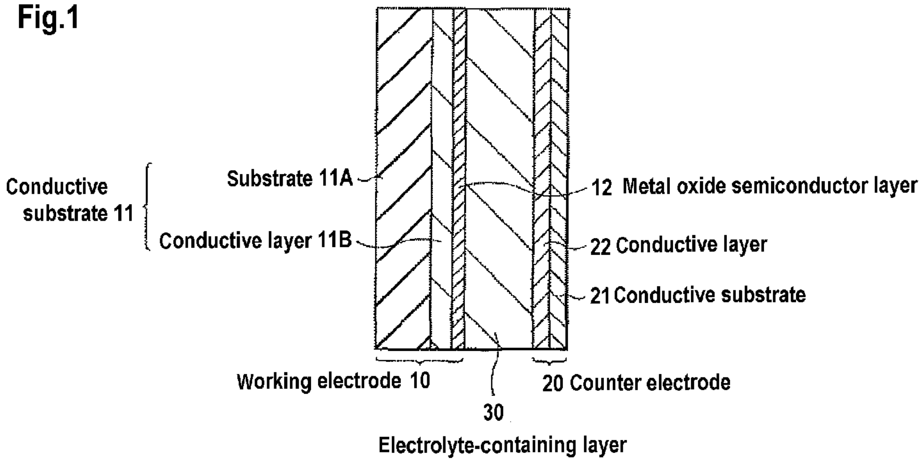
FIG. 1 is a schematic diagram showing the cross-sectional structure of an example of the photoelectric conversion device of the invention.

Hereinafter, the novel compound of the invention, the support material carrying the novel compound, and the photoelectric conversion device produced using the support material will be described with reference to preferred embodiments.

First, the novel compound of the invention (hereinafter also referred to as the compound of the invention) will be described.

In formula (1), the group represented by A is a divalent group which is an optionally substituted aromatic hydrocarbon ring group or an optionally substituted aromatic heterocyclic group.

Examples of the aromatic hydrocarbon ring group include an unsubstituted aromatic hydrocarbon ring group, an aliphatic hydrocarbon group-substituted aromatic hydrocarbon ring group, etc. Examples of the aromatic heterocyclic group include an unsubstituted aromatic heterocyclic group, an aliphatic hydrocarbon group-substituted aromatic heterocyclic group, etc.

Examples of the divalent unsubstituted aromatic hydrocarbon ring group include 1,2-phenylene, 1,3-phenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, anthracene-1,4-diyl, anthracene-1,5-diyl, anthracene-1,10-diyl, anthracene-9,10-diyl, perylene-3,9-diyl, perylene-3,10-diyl, pyrene-1,6-diyl, pyrene-2,7-diyl, etc.

For example, the aliphatic hydrocarbon group-substituted divalent aromatic hydrocarbon ring group may have one to three aliphatic hydrocarbon groups of 1 to 20 carbon atoms as substituents on the divalent unsubstituted aromatic hydrocarbon ring.

Examples of the aliphatic hydrocarbon group of 1 to 20 carbon atoms include linear, branched, and cyclic alkyl groups such as methyl, ethyl, propyl, isopropyl, butyl, sec-butyl, tert-butyl, isobutyl, amyl, isoamyl, tert-amyl, hexyl, heptyl, isoheptyl, tert-heptyl, n-octyl, isooctyl, tert-octyl, nonyl, cyclopropyl, cyclobutyl, cyclopentyl, cyclohexyl, cycloheptyl, cyclooctyl, cyclononyl, and cyclodecyl. The aliphatic hydrocarbon group of 1 to 20 carbon atoms may be intervened by —O—, —COO—, —OCO—, —CO—, —S—, —SO—, $—SO_2—$, —NR6-, —C═C—, or —C≡C—, wherein R6 is an aliphatic hydrocarbon group of 1 to 20 carbon atoms, which may be exemplified by the same groups as the above aliphatic hydrocarbon group of 1 to 20 carbon atoms. When the intervening group has one or more carbon atoms, the total number of carbon atoms, including those in the intervening group, is from 1 to 20.

Examples of the divalent unsubstituted aromatic heterocyclic group include furan-2,5-diyl, furan-3,5-diyl, thiophene-2,5-diyl, thiophene-3,5-diyl, 2H-chromene-3,7-diyl, benzothiophene-2,6-diyl, benzothiophene-2,5-diyl, etc.

Examples of the aliphatic hydrocarbon group-substituted divalent aromatic heterocyclic group include 1-alkyl-pyrrole-2,5-diyl, 1-alkyl-pyrrole-3,5-diyl, and a group having one to three aliphatic hydrocarbon groups of 1 to 20 carbon atoms as substituents on the divalent unsubstituted aromatic heterocyclic group. The aliphatic hydrocarbon group of 1 to 20 carbon atoms may be exemplified by the same groups as the above aliphatic hydrocarbon group of 1 to 20 carbon atoms.

The aromatic hydrocarbon ring groups or the aromatic heterocyclic groups listed above may further have a substituent(s). The aromatic hydrocarbon ring groups and the aromatic heterocyclic groups may be substituted with groups such as a fluorine atom, a chlorine atom, a bromine atom, an iodine atom, a cyano group, a nitro group, a hydroxyl group, a thiol group, and an —NR7R8 group. R7 and R8 represent the same groups as represented by R7 and R8, respectively, in formulae (B-1) to (B-13) shown below. When the aromatic hydrocarbon ring group or the aromatic heterocyclic group has a methylene moiety, its two hydrogen atoms may be replaced by one oxygen atom to form carbonyl.

In formula (1), B represents a group including a chain of one to four pieces of one or more groups selected from the groups represented by formulae (B-1) to (B-13), preferably a group including a chain of two to four pieces of one or more groups selected from the groups represented by formulae (B-1) to (B-13). Pieces of each group represented by any of formulae (B-1) to (B-13) may be linked in any direction. The mark * in the group represented by each of formulae (B-1) to (B-13) indicates the position to which the adjacent group is to be linked (the same applies hereinafter).

In formulae (B-1) to (B-13), X represents S, O, or NR, wherein R represents an optionally substituted hydrocarbon group. Examples of the optionally substituted hydrocarbon group represented by R are the same as those of the optionally substituted hydrocarbon group represented by R1, R2, and R3 described below.

Any hydrogen atom in the groups represented by formulae (B-1) to (B-13) may be replaced by a fluorine atom, a chlorine atom, a bromine atom, an iodine atom, a cyano group, a nitro group, a hydroxyl group, a thiol group, an —NR7R8 group, or an optionally substituted aliphatic hydrocarbon group, wherein R7 and R8 each represent an optionally substituted hydrocarbon group. Groups as substituents on each of the B groups may be linked together to form a ring.

For example, the optionally substituted aliphatic hydrocarbon group may be the above aliphatic hydrocarbon group of 1 to 20 carbon atoms, and the groups may be substituted with the substituents listed above for the aromatic hydrocarbon ring group and the aromatic heterocyclic group.

Examples of the optionally substituted hydrocarbon groups represented by R7 and R8 are the same as those of the optionally substituted hydrocarbon groups represented by R1, R2, and R3 described below.

Examples of the A-B moiety in formula (1) include A-B(1) to A-B(35) shown below. In each of the examples of the A-B moiety shown below, the ring structure at the left end corresponds to A, and the other part corresponds to B.

Although the examples shown below have no substituent, the A moiety may have a substituent(s) as mentioned above, and any hydrogen atom in the B moiety may be replaced by a substituent as mentioned above. In each of A-B(16) to A-B(23) shown below, each bond drawn across two or more rings means that any of the carbon atoms in these rings may form a bond (the same applies hereinafter).

A-B(1)

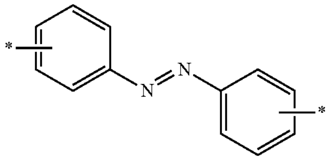

A-B(2)

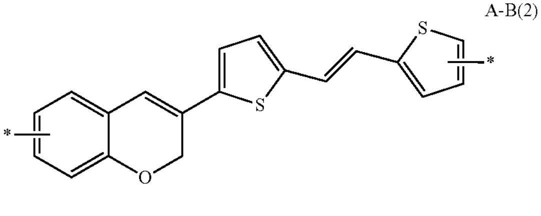

-continued

A-B(3)

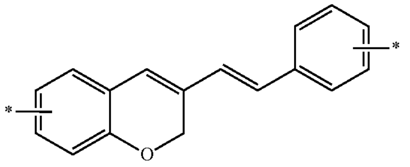

A-B(4)

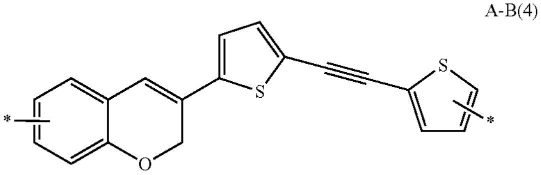

A-B(5)

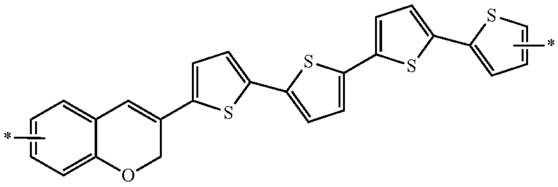

A-B(6)

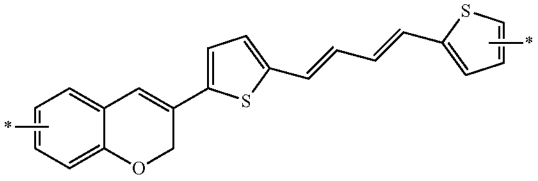

A-B(7)

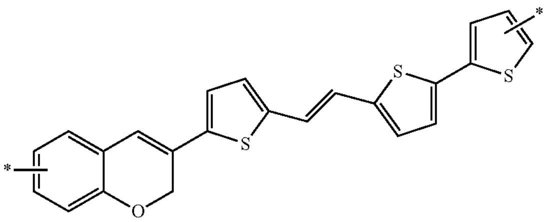

A-B(8)

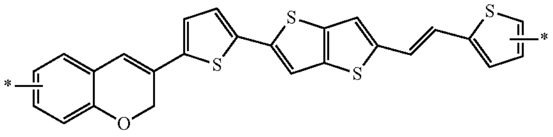

A-B(9)

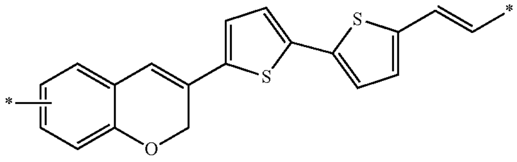

A-B(10)

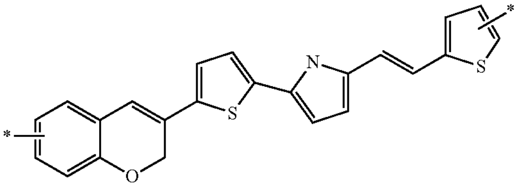

-continued
A-B(11)
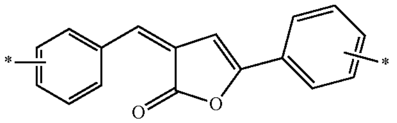
A-B(12)
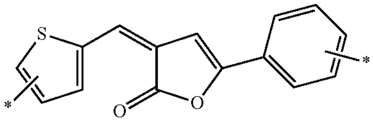
A-B(13)
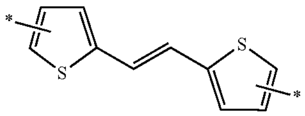
A-B(14)
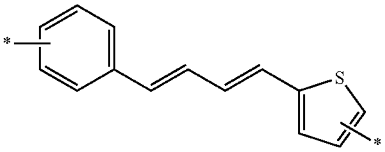
A-B(15)
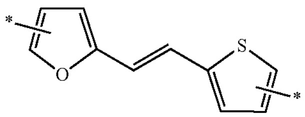
A-B(16)
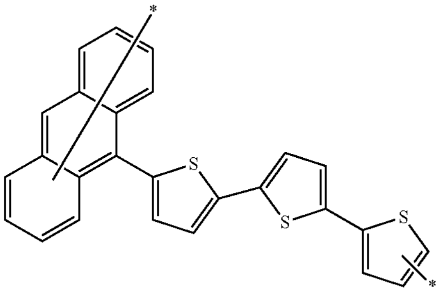
A-B(17)
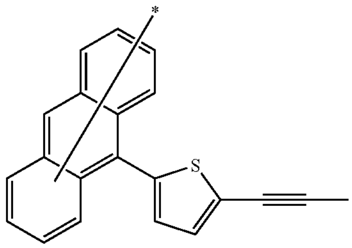
A-B(18)
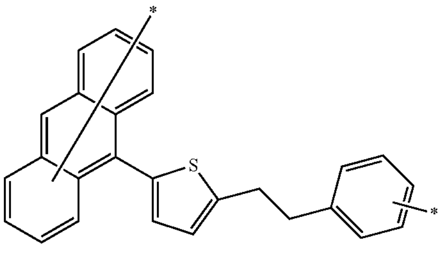
-continued
A-B(19)
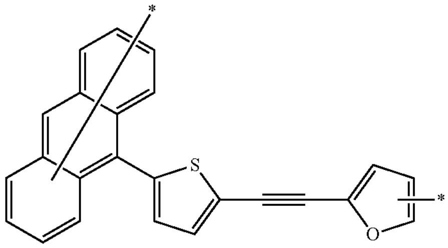
A-B(20)
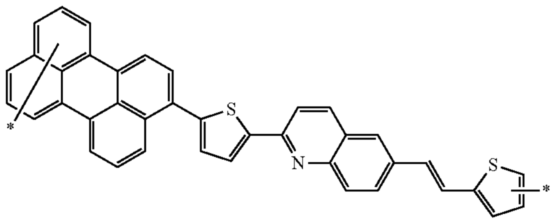
A-B(21)
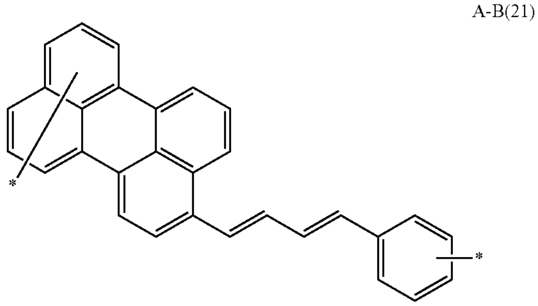
A-B(22)
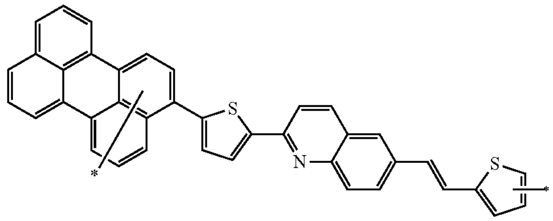
A-B(23)
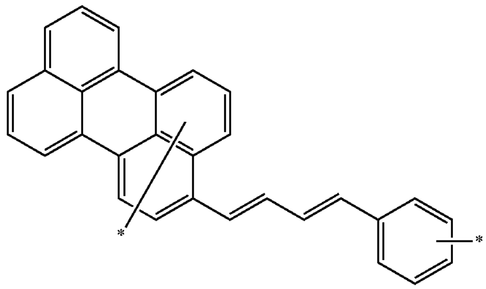
A-B(24)
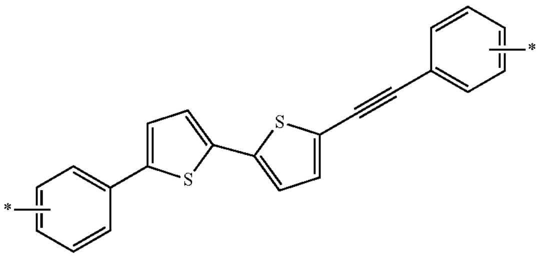

-continued

A-B(25)

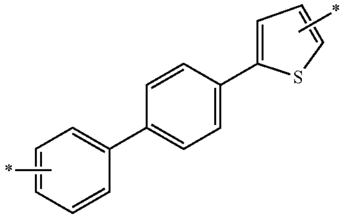

A-B(26)

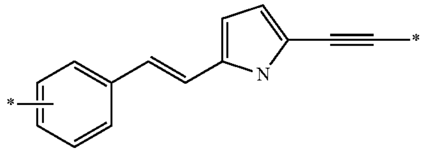

A-B(27)

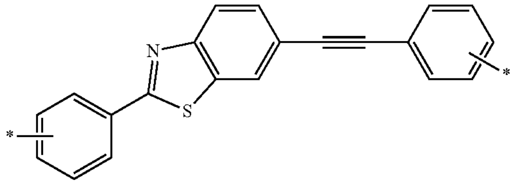

A-B(28)

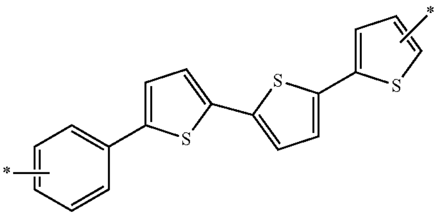

A-B(29)

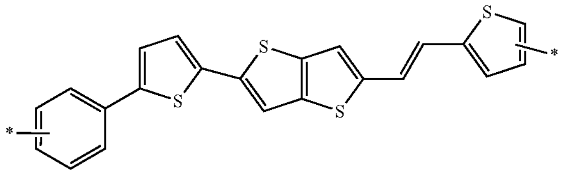

A-B(30)

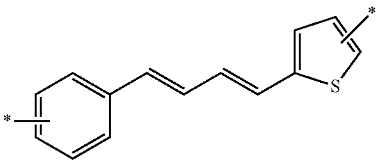

A-B(31)

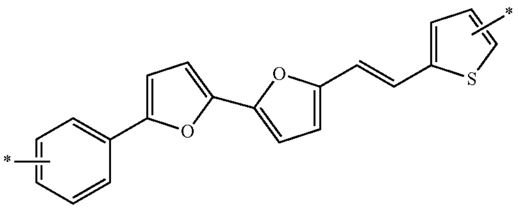

A-B(32)

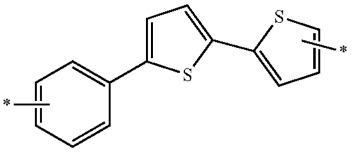

-continued

A-B(33)

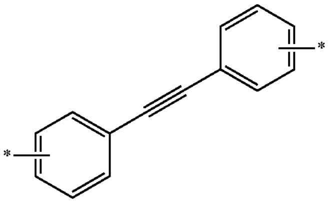

A-B(34)

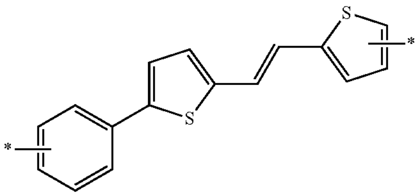

A-B(35)

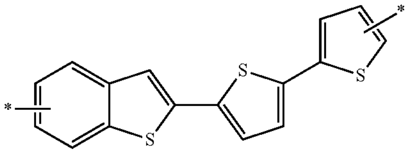

In formula (1), the hydrocarbon group of the optionally substituted hydrocarbon group represented by R1, R2, and R3 may be an aromatic hydrocarbon group, an aliphatic hydrocarbon group-substituted aromatic hydrocarbon group, an aliphatic hydrocarbon group, or the like.

The aromatic hydrocarbon group may be phenyl, naphthyl, cyclohexylphenyl, biphenyl, terphenyl, fluorenyl, thiophenylphenyl, furanylphenyl, 2'-phenyl-propylphenyl, benzyl, naphthylmethyl, or the like. For example, the aliphatic hydrocarbon group may be an aliphatic hydrocarbon group of 1 to 20 carbon atoms as described above for A. The aliphatic hydrocarbon group-substituted aromatic hydrocarbon group may be phenyl, naphthyl, benzyl or the like substituted with the aliphatic hydrocarbon group.

These hydrocarbon groups may be substituted with a substituent such as a fluorine atom, a chlorine atom, a bromine atom, an iodine atom, a cyano group, a nitro group, a hydroxyl group, a thiol group, or an —NR7R8 group, wherein R7 and R8 represent the same groups as R7 and R8 described above for B.

In formula (1), the optionally substituted hydrocarbonoxy group represented by R1, R2, and R3 may has an optionally substituted hydrocarbon moiety, which can be exemplified by the same groups as the optionally substituted hydrocarbon group represented by R1 described above, and an —O— moiety, which is interposed between the hydrocarbon moiety and the Si atom.

At least one of R1, R2, and R3 represents an optionally substituted hydrocarbon oxy group. In terms of the high ability to adsorb to the support described below, it is preferable that at least one of R1, R2, and R3 is an aliphatic hydrocarbonoxy group, or all of R1, R2, and R3 are optionally substituted hydrocarbonoxy groups. It is more preferable that two or three of R1, R2, and R3 are each a linear or branched aliphatic hydrocarbonoxy group (especially of 1 to 5 carbon atoms), and none or one of them is a linear or branched aliphatic hydrocarbon group (especially of 1 to 5 carbon atoms). It is most preferable that all of R1, R2, and R3 are each a linear or branched aliphatic hydrocarbonoxy group (especially of 1 to 5 carbon atoms).

In formula (1), the optionally substituted hydrocarbon group represented by R4 and R5 may be the group described above for R1. R4 and R5 may be linked together to form a ring, or R4 and R5 may be each independently linked with A to form a ring.

In the compound represented by formula (1), the partial structure (2) shown below is preferably any one of the partial structures (2-1) to (2-4) shown below, so that the compound can have particularly good properties for photoelectric conversion applications. The compound having the partial structure (2-1) or (2-2) shown below is particularly preferred because it is easy to produce and has high efficiency of electron injection into the support.

In the partial structures (2) and (2-1) to (2-4) shown below, the bond of A to B is omitted. In the partial structures (2-1) to (2-4) shown below, any carbon atom of the aromatic hydrocarbon ring and the aromatic heterocyclic ring may form the bond of A to B.

(2)

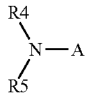

wherein A, R4, and R5 have the same meanings as in formula (1).

(2-1)

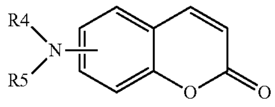

(2-2)

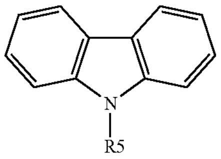

(2-3)

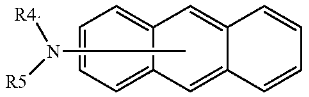

(2-4)

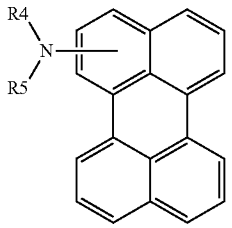

wherein R4 and R5 have the same meanings as in formula (1).

The compound represented by formula (1) is preferably a compound having the partial structure (3-1) or (3-2) as the partial structure (3) shown below because such a compound is easy to produce and has good properties for photoelectric conversion applications.

In the partial structures (3), (3-1), and (3-2) shown below, the bond of B to the Si atom is omitted. In the partial structures (3-1) and (3-2), any carbon atom in the ring structure at the right end may form the bond of B to the Si atom.

(3)

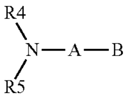

wherein A, B, R4, and R5 have the same meanings as in formula (1).

(3-1)

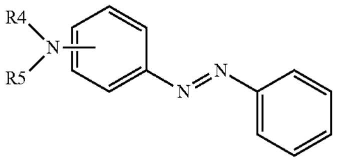

(3-2)

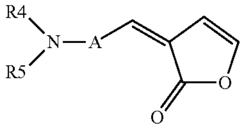

wherein A, R4, and R5 have the same meanings as in formula (1).

The compound represented by formula (1) preferably satisfies at least one of the following conditions (i) to (iii):

(i) the group represented by B has at least one piece of the group represented by any one of formulae (B-1) to (B-9) and (B-11) to (B-13) shown above;

(ii) R4 and R5 are each an optionally substituted hydrocarbon group of 1 to 12 carbon atoms; and (iii) at least one of R4 and R5 is linked with A to form a ring.

The compound satisfying the condition (i) is preferable in that it has particularly high efficiency of electron injection into the support. The compound satisfying the condition (ii) is preferable in that it is easy to produce and that a particularly large number of moles of it can be adsorbed to the support. The compound satisfying the condition (iii) is preferable in that it can provide particularly high durability to photoelectric conversion devices.

Specific examples of the compound represented by formula (1) include compounds Nos. 1 to 68 shown below. It will be understood that these compounds are non-limiting examples of the novel compound of the invention. In the formulae, Me represents methyl, Et ethyl, Bu butyl, Pr propyl, Pen pentyl, Hex hexyl, Dec decyl, and Ph phenyl.

NO. 1
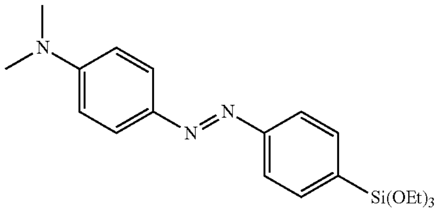
No. 2
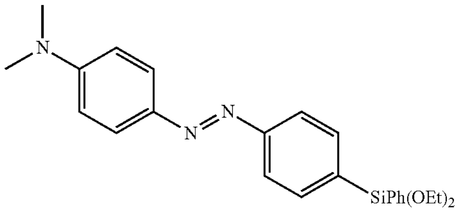
No. 3
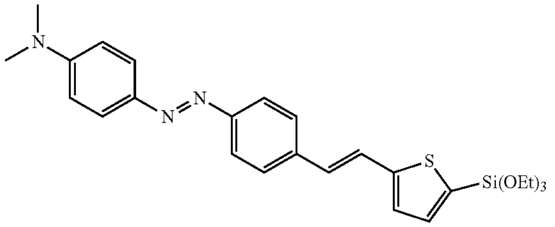
NO. 4
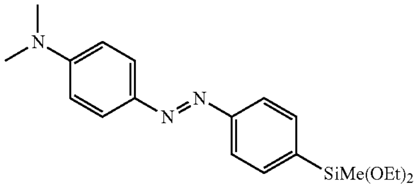
No. 5
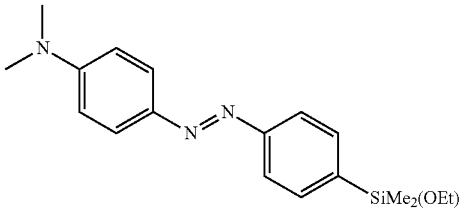
NO. 6
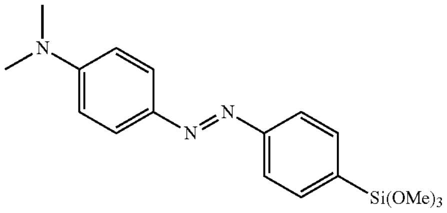
No. 7
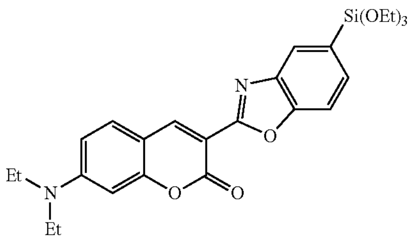
No. 8
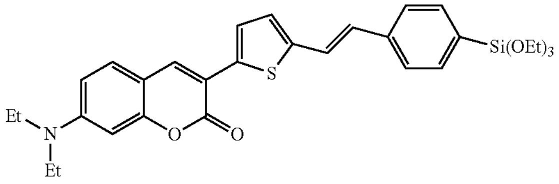
No. 9
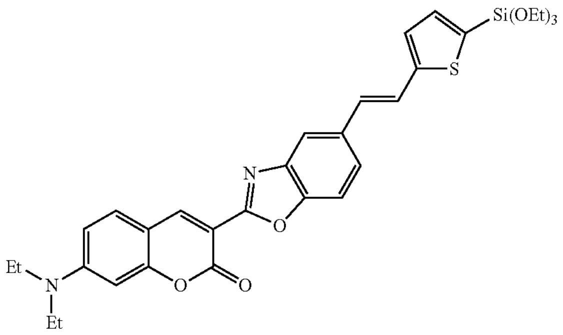
No. 10
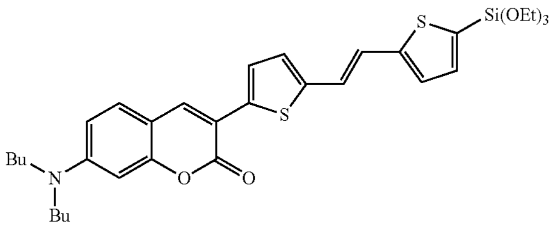
No. 11
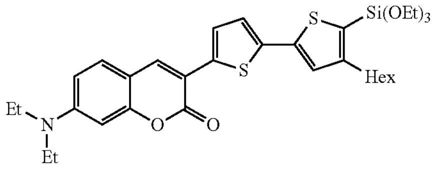
No. 12
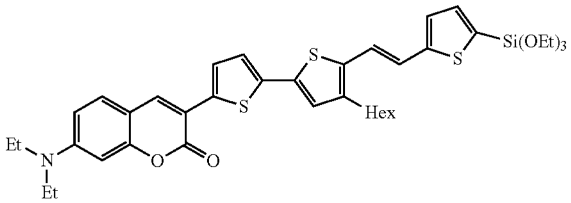

-continued
No. 13
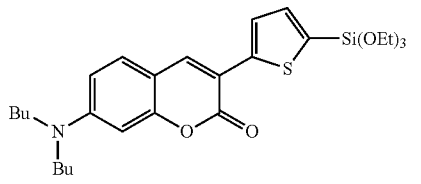
No.14
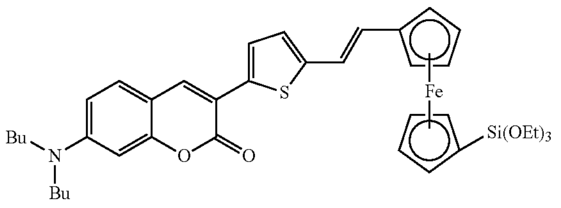
No. 15
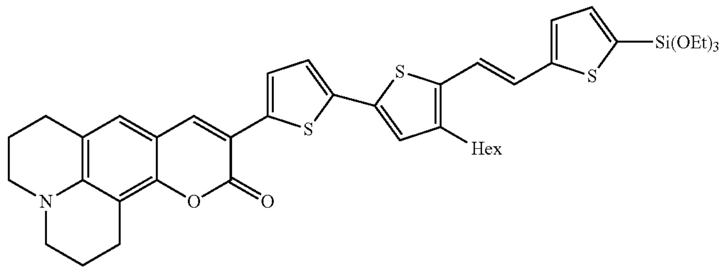
No. 16
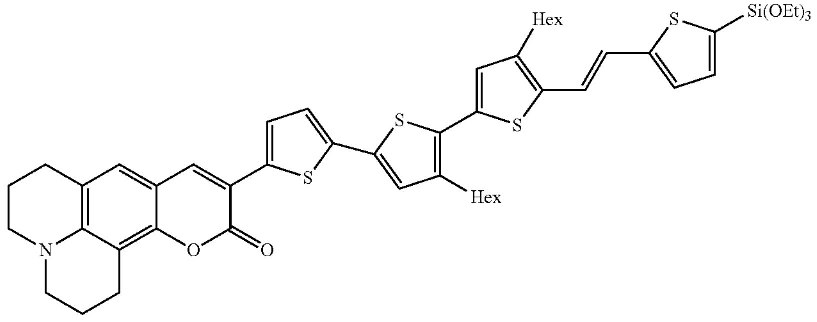
No. 17
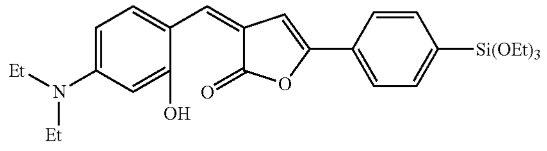
No. 18
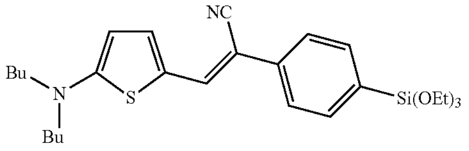
No. 19
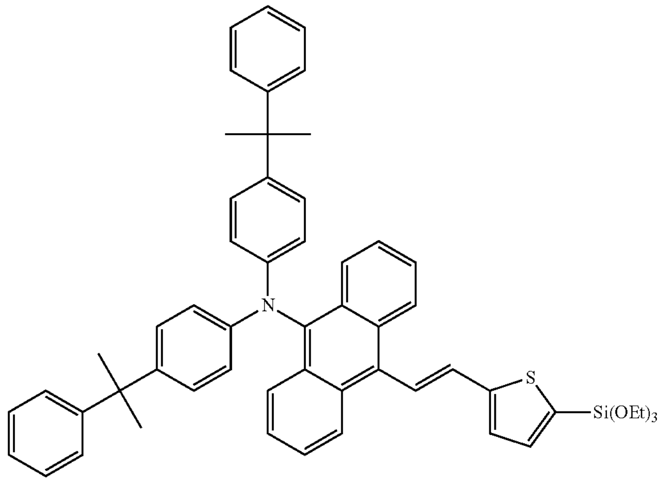

-continued
No. 20
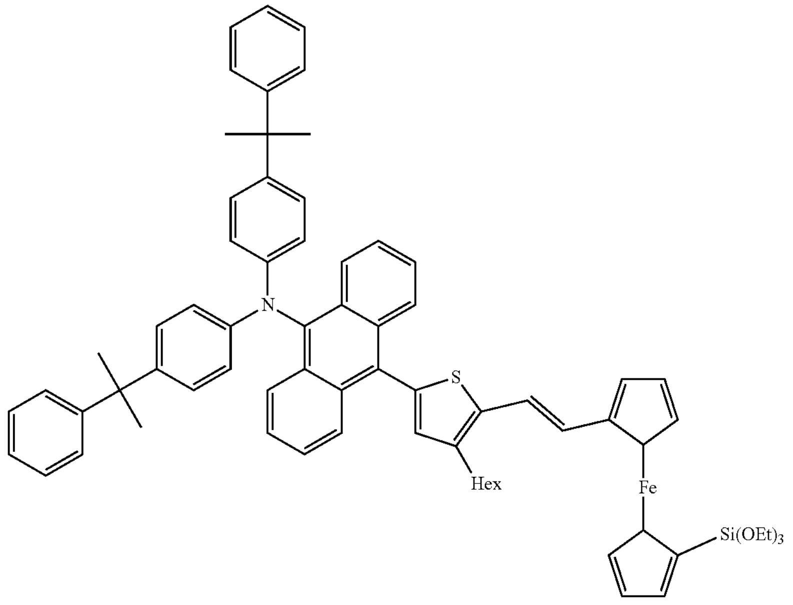
No. 21
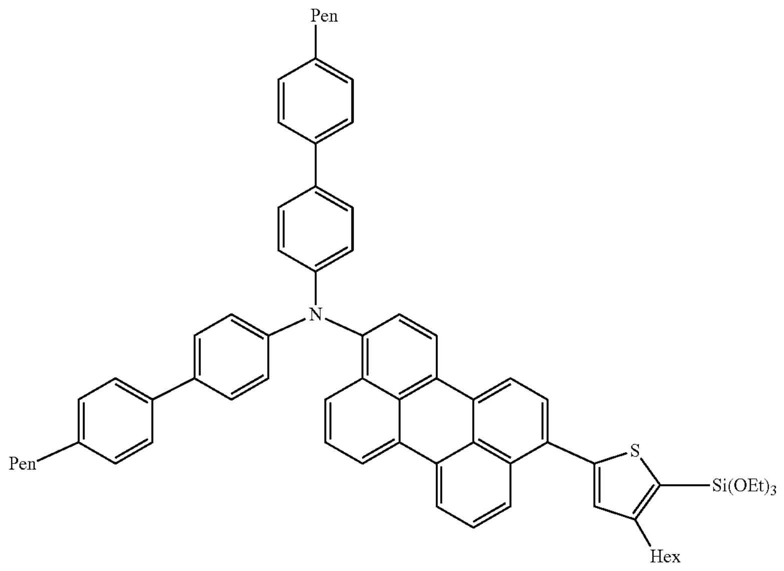
No. 22
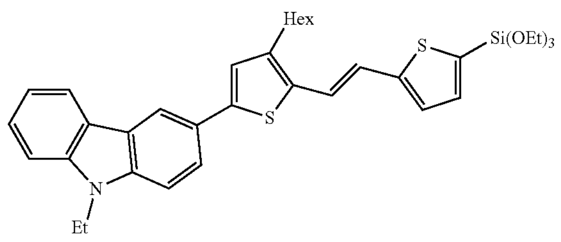
No. 23
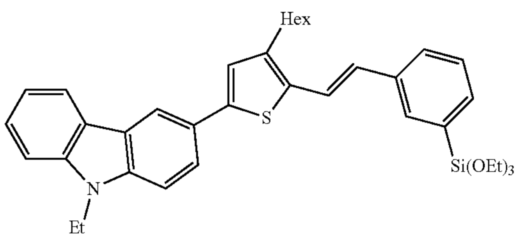

-continued
No. 24
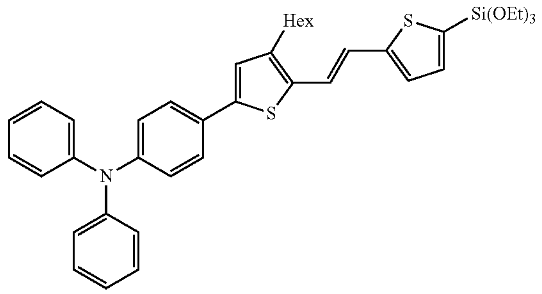
No. 25
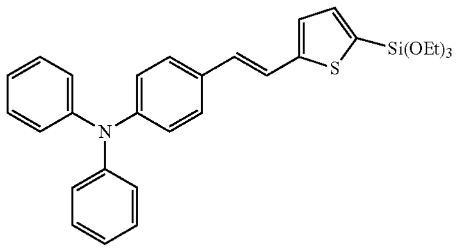
No. 26
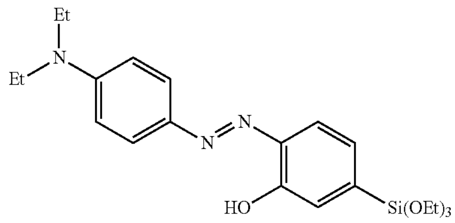
No. 27
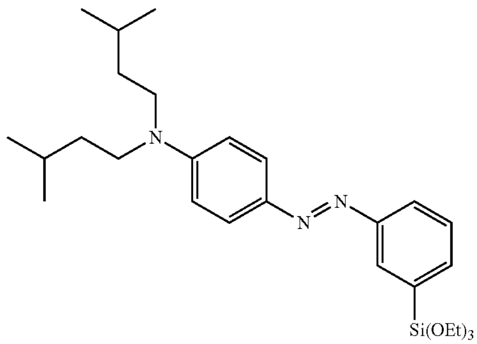
No. 28
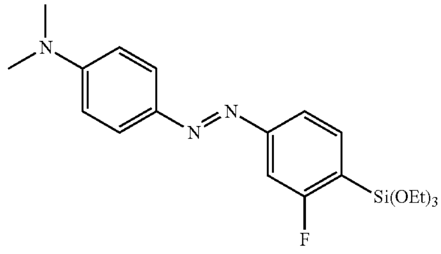
No. 29
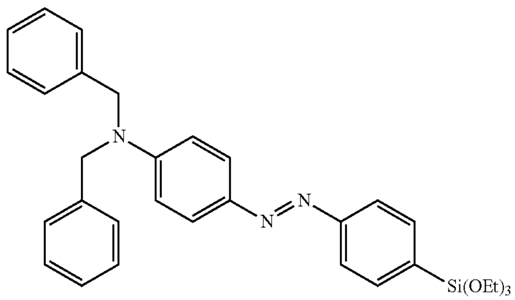
No. 30
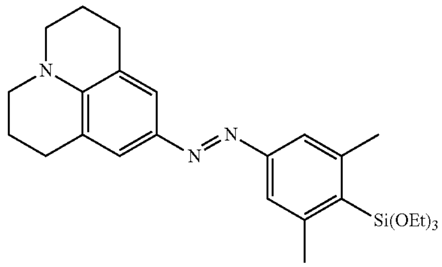
No. 31
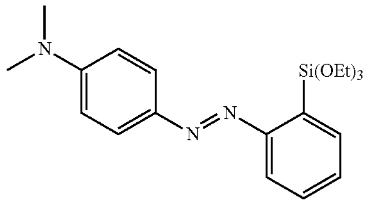

-continued
No. 32
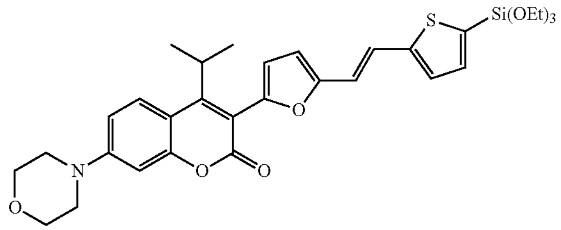
No. 33
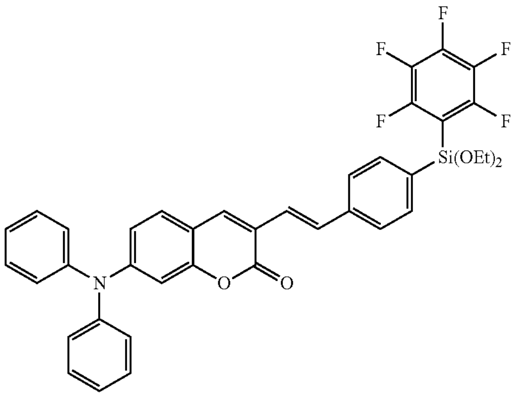
No. 34
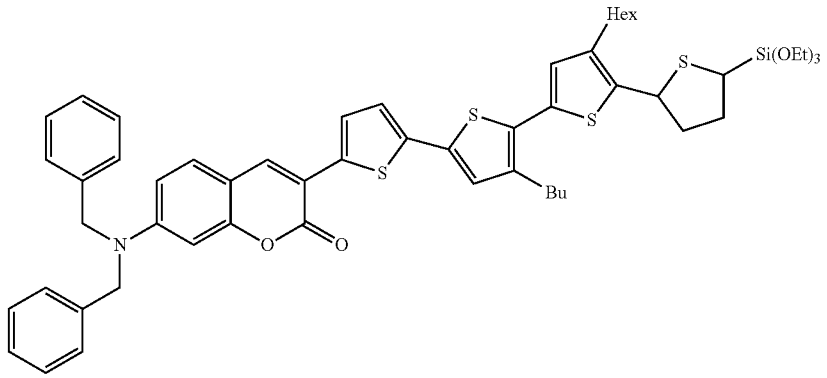
No. 35
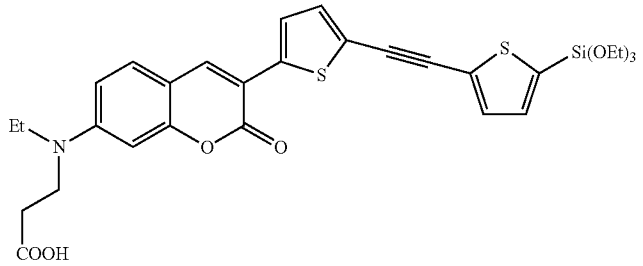
No. 36
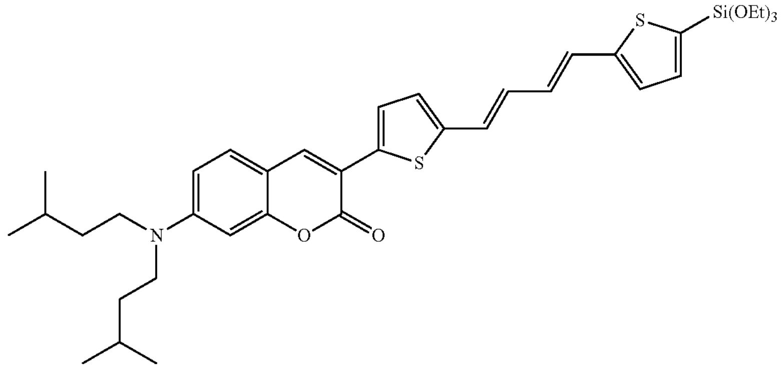

-continued
No. 37
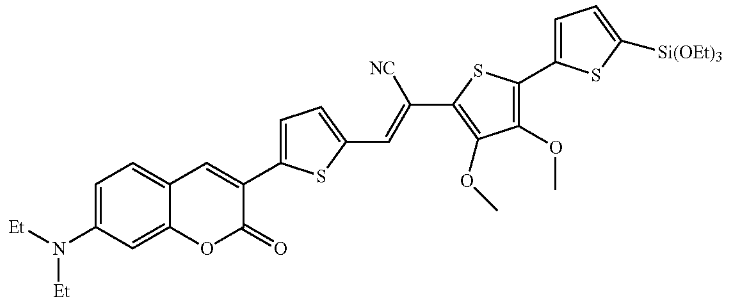
No. 38
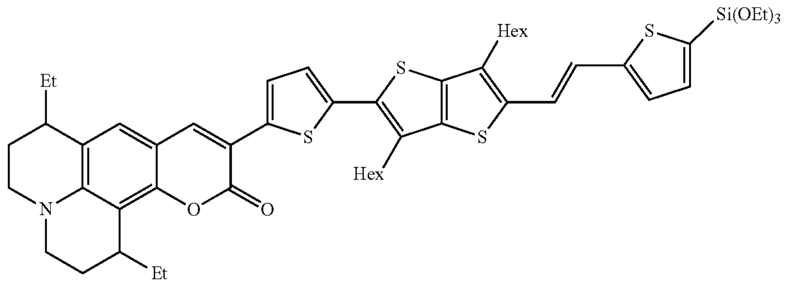
No. 39
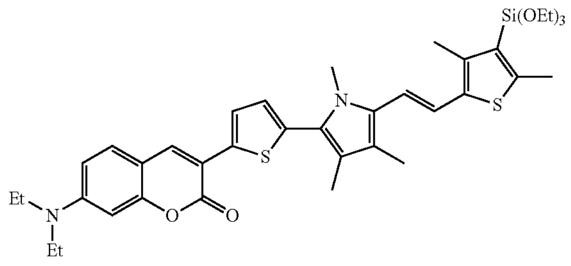
No. 40
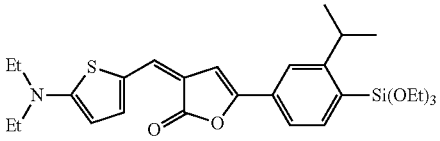
No. 41
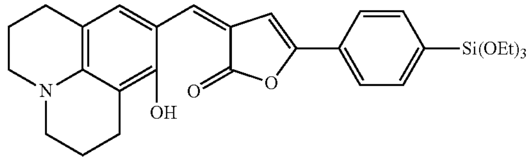
No. 42
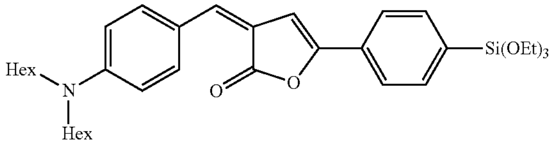
No. 43
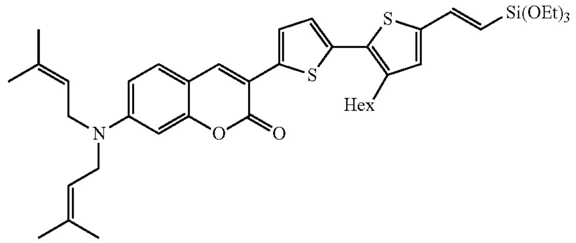
No. 44
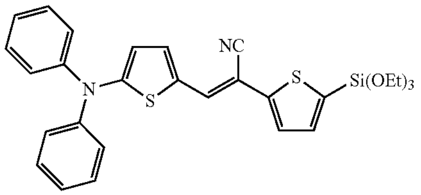

-continued
No. 45
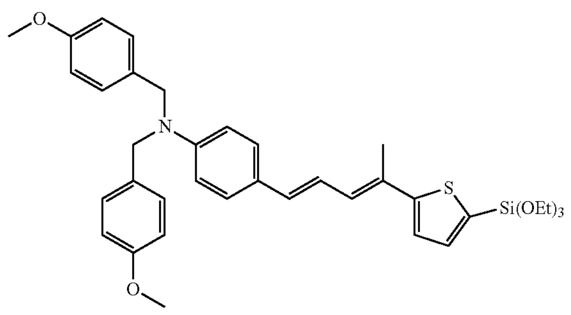
No. 46
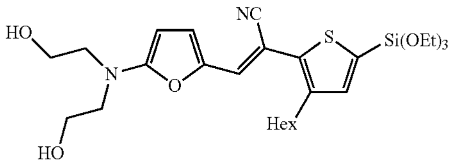
No. 47
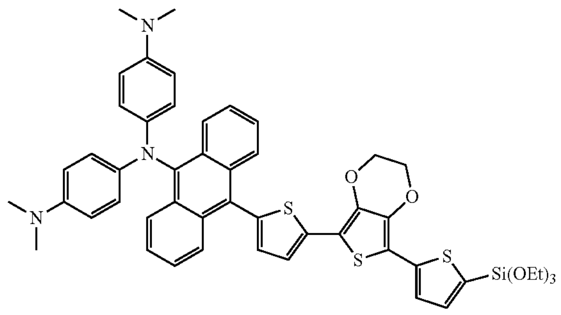
No. 48
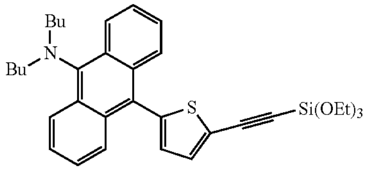
No. 49
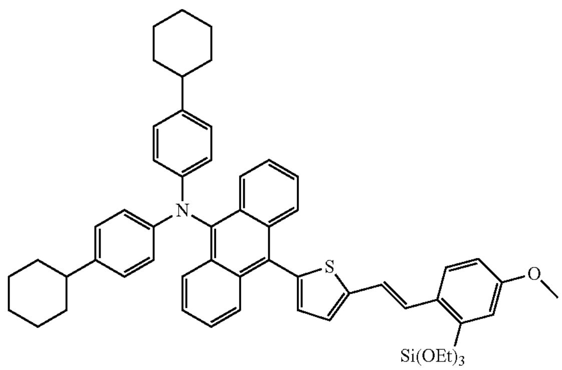
No. 50
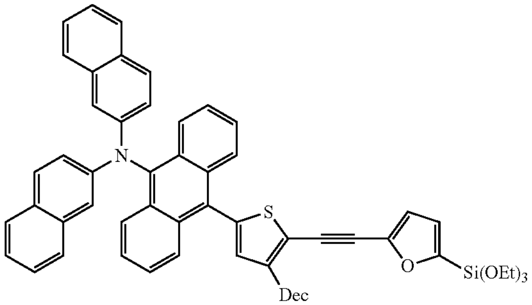
No. 51
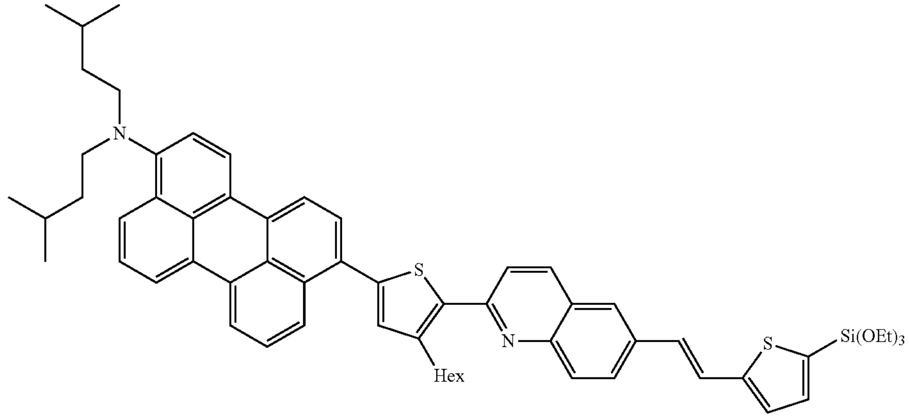

-continued
No. 52
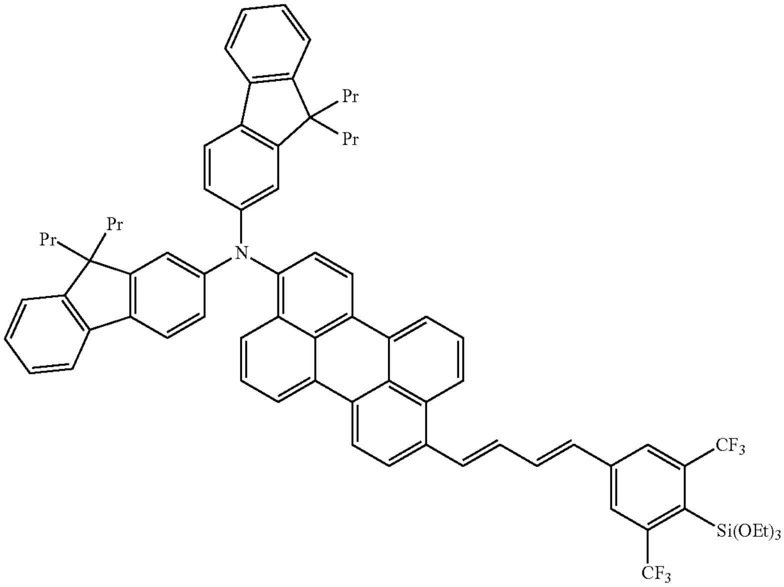
No. 53
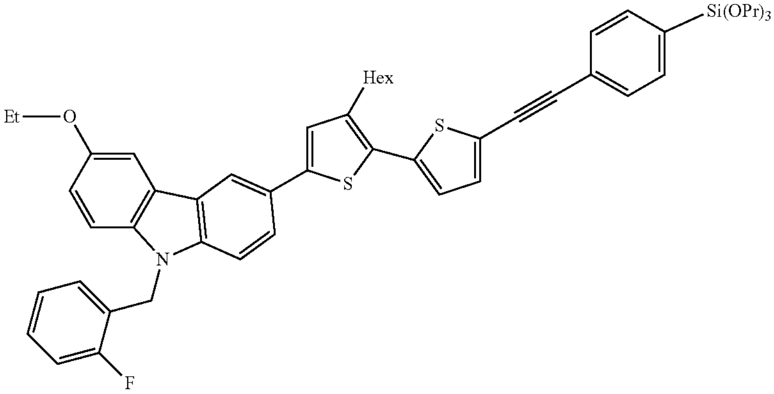
No.54
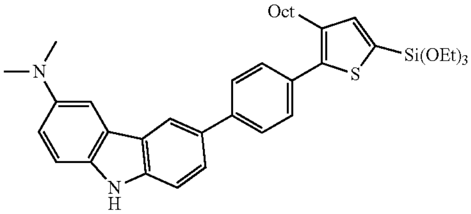
No.55
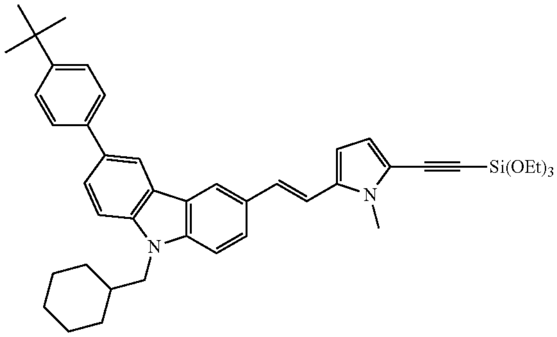

-continued
No.56
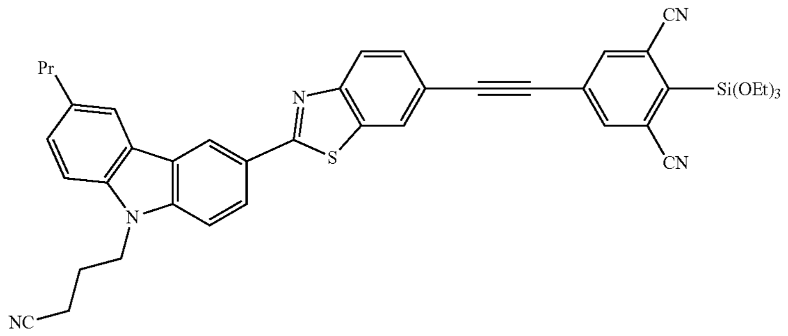
NO.57
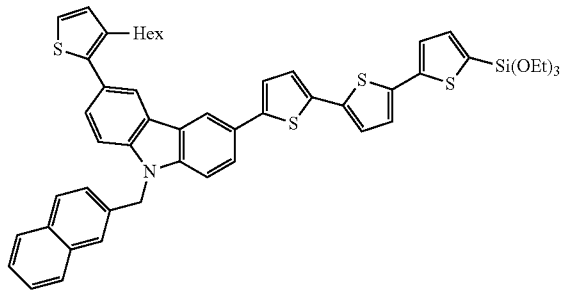
No.58
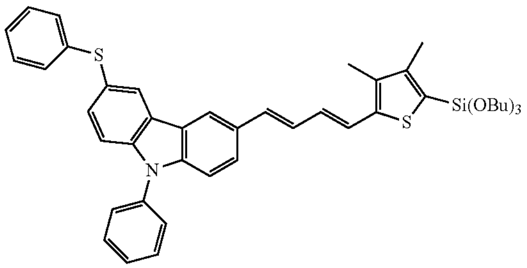
No.59
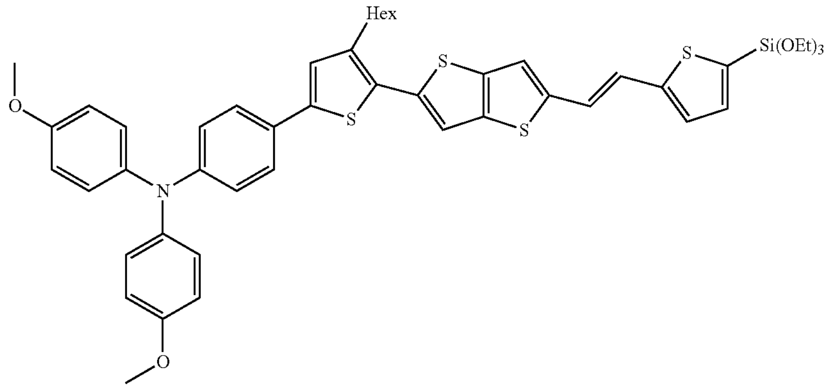
No.60
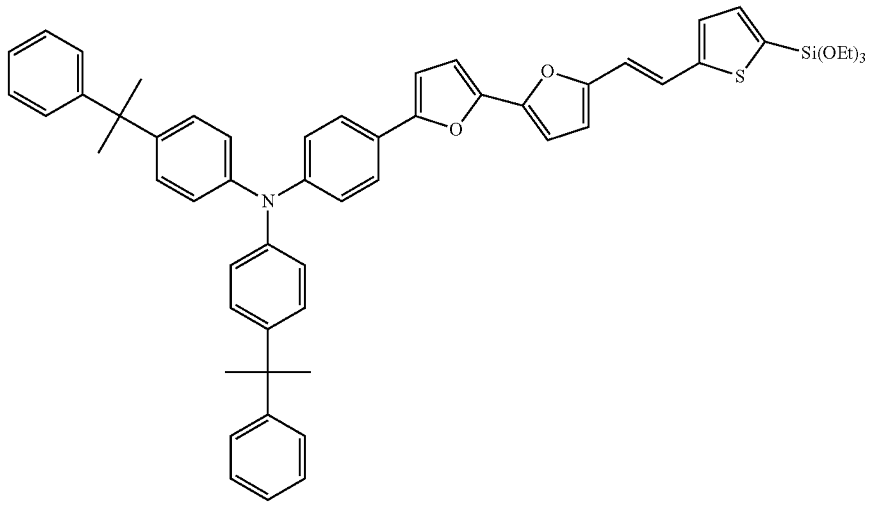

-continued

No. 61

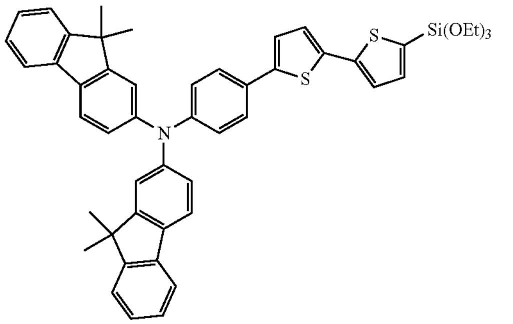

No.62

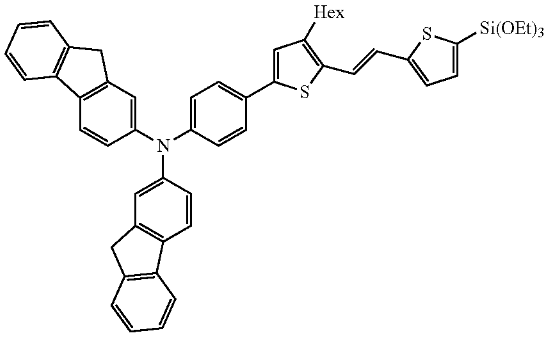

No.63

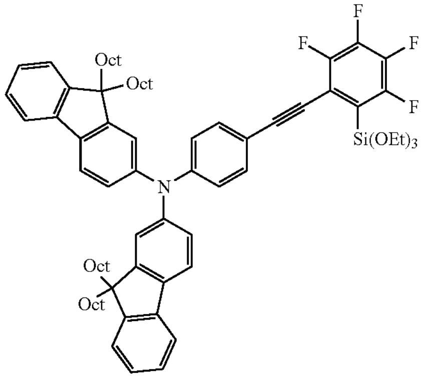

No.64

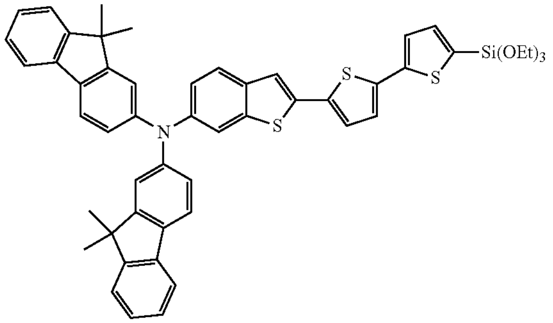

No.65

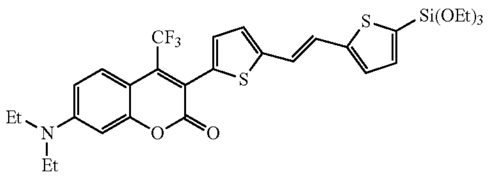

No.66

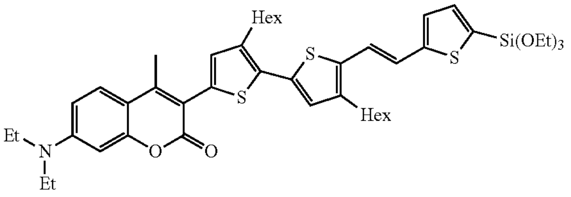

No.67

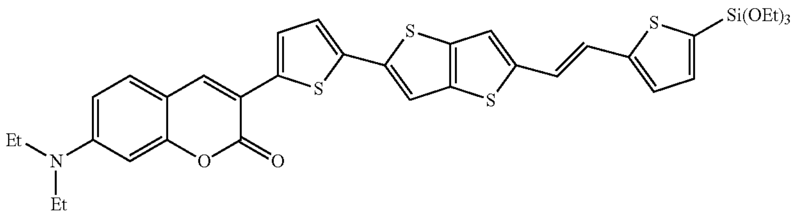

No.68

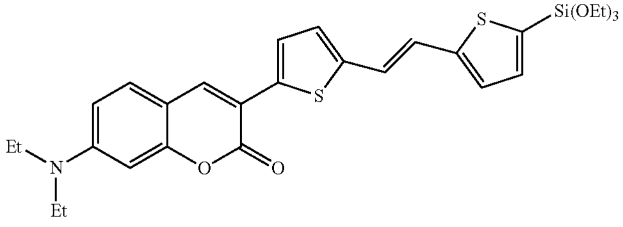

The novel compound of the invention can be obtained by a method based on known or well-known general reactions, and the method for synthesizing it is not restricted. A typical example of the synthetic method includes allowing a halide (11) to react with a silylating agent (12) as shown in reaction formula (A) below, which enables the synthesis of the novel compound of the invention represented by formula (1). The catalyst, the ligand, and the base may be changed as needed.

Reaction formula (A)

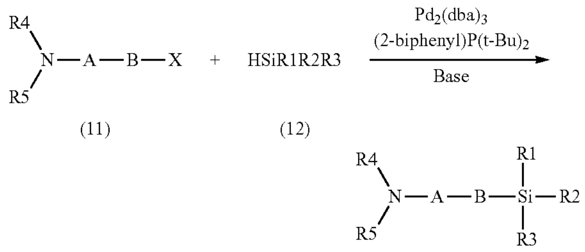

(11) (12)

(1)

In the formula, A, B, and R1 to R5 represent the same groups as those in formula (1), X represents a halogen atom, and dba represents a dibenzylideneacetone ligand.

As described below, the novel compound of the invention may be supported on a support, and such a support material carrying the novel compound of the invention is advantageously used in applications such as photoelectric conversion devices. The novel compound of the invention can also be used in other applications such as synthetic intermediates for optical recording materials, pharmaceuticals, agricultural chemicals, perfumes, dyes, etc.; a variety of functional materials and raw materials for polymers; photoelectrochemical cells, non-linear optical devices, electrochromic displays, holograms, organic semiconductors, and organic ELs; silver halide photographic materials, photosensitizers; colorants for use in printing ink, inkjet printing, electrophotographic color toners, cosmetics, and plastics; protein staining agents and luminescent dyes for use in detection of substances; and raw materials for synthetic quartz, paints, synthetic catalysts, catalyst supports, surface coating thin film materials, silicone rubber crosslinking agents, and thickening and binding agents.

Next, the support material of the invention carrying the novel compound of the invention will be described.

Examples of the material (support) for use in the support material of the invention include organic resins such as acrylic resins and fluororesins, metal oxides such as titanium oxide, zinc oxide, and aluminum oxide, silicon oxide, zeolite, activated carbon, etc, which preferably have a porous surface. The novel compound of the invention has high adsorption ability to a support because it has an alkoxysilyl group. The compound of the invention can be supported on a support using a known method such as gas-phase adsorption or liquid-phase adsorption. An example of liquid-phase adsorption includes dissolving the compound of the invention in a solvent and immersing the support in the solution so that the compound is adsorbed to the support.

The support may be in any shape. For example, the shape of the support may be appropriately selected from film shape, powdery shape, granular shape, or other shapes, depending on the intended use of the support. The size of the support and the amount of the compound of the invention supported on the support are also not restricted, and they may be appropriately selected depending on the intended use of the support.

The support material of the invention carrying the novel compound of the invention can be advantageously used in the photoelectric conversion device described below and also be used for catalysts, toners, and other materials.

Next, the photoelectric conversion device of the invention will be described.

The photoelectric conversion device of the invention is a dye-sensitized photoelectric conversion device, which may be the same as a conventional dye-sensitized photoelectric conversion device except that the novel compound of the invention is used therein as a dye. Hereinafter, a typical example of the structure of the photoelectric conversion device of the invention will be described with reference to FIGS. 1 and 2.

Figure 2:
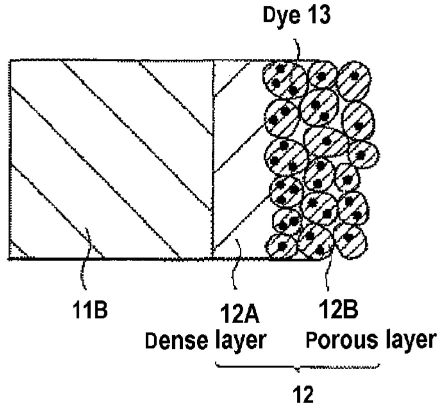
FIG. 2 is an enlarged diagram of the principal part of the photoelectric conversion device of the invention shown in FIG. 1.

FIG. 1 schematically shows the cross-sectional structure of an example of the photoelectric conversion device of the invention. FIG. 2 extracts and shows in an enlarged manner the principal part of the photoelectric conversion device shown in FIG. 1. The photoelectric conversion device shown in FIGS. 1 and 2 corresponds to the principal part of what is called a dye-sensitized solar cell. The photoelectric conversion device has a working electrode 10 and a counter electrode 20, which are opposed to each other with an electrolyte-containing layer 30 interposed therebetween, in which at least one of the working electrode 10 and the counter electrode 20 is an optically-transparent electrode.

For example, the working electrode 10 includes a conductive substrate 11, a metal oxide semiconductor layer 12 provided on one surface (the counter electrode 20-side surface) of the substrate 11, and a dye 13 supported on the metal oxide semiconductor layer 12. In the photoelectric conversion device of the invention, the dye 13 corresponds to the novel compound of the invention represented by formula (1), and the metal oxide semiconductor layer 12 carrying the dye (the novel compound of the invention) corresponds to the support material of the invention.

The working electrode 10 functions as a negative electrode for the external circuit. For example, the conductive substrate 11 includes an insulating substrate 11A and a conductive layer 11B provided on the surface of the substrate 11A.

For example, the substrate 11A may be made of an insulating material such as glass or plastic. For example, plastic is used in the form of a transparent polymer film. Examples of plastic used to form a transparent polymer film include tetraacetyl cellulose (TAC), polyethylene terephthalate (PET), polyethylene naphthalate (PEN), syndiotactic polystyrene (SPS), polyphenylene sulfide (PPS), polycarbonate (PC), polyarylate (PAR), polysulfone (PSF), polyestersulfone (PES), polyetherimide (PEI), cyclic polyolefin, brominated phenoxy resin, etc.

Examples of the conductive layer 11B include a conductive metal oxide thin film including indium oxide, tin oxide, indium-tin complex oxide (ITO), fluorine-doped tin oxide (FTO: F—$SnO_2$), or the like; a metal thin film including gold (Au), silver (Ag), platinum (Pt), or the like; and a layer made of a metal mesh, a conductive polymer, or the like.

Alternatively, for example, the conductive substrate 11 may be a monolayer structure made of a conductive material. In this case, the conductive substrate 11 is typically made of a conductive metal oxide such as indium oxide, tin oxide, indium-tin complex oxide, or fluorine-doped tin oxide, a metal such as gold, silver, or platinum, or a conductive polymer.

The metal oxide semiconductor layer 12 is a support, on which the dye 13 is supported, and, for example, has a porous structure as shown in FIG. 2. The metal oxide semiconductor layer 12 includes a dense layer 12A and a porous layer 12B. The dense layer 12A, which is formed at the interface with the conductive substrate 11, is preferably dense and less-porous, more preferably in the form of a film. The porous layer 12B, which is formed at the surface in contact with the electrolyte-containing layer 30, preferably has a structure with a large number of pores and a large surface area, and more preferably a porous structure made of deposited fine particles. Alternatively, for example, the metal oxide semiconductor layer 12 may be formed to have a film-shaped monolayer structure. As used herein, the term “carrying” or “supported on” refers to a state in which the dye 13 is chemically, physically, or electrically bonded or adsorbed to the porous layer 12B.

For example, the material (metal oxide semiconductor material) included in the metal oxide semiconductor layer 12 may be titanium oxide, zinc oxide, tin oxide, niobium oxide, indium oxide, zirconium oxide, tantalum oxide, vanadium oxide, yttrium oxide, aluminum oxide, or magnesium oxide. Titanium oxide and zinc oxide are particularly preferred as the metal oxide semiconductor material in that they can yield high conversion efficiency. Any of these metal oxide semiconductor materials may be used alone or in combination of two or more (as a mixture, a mixed crystal, a solid solution, a surface coating, or the like). For example, titanium oxide may be used in combination with zinc oxide or the like.

The metal oxide semiconductor layer 12 having a porous structure may be formed using a method such as an electrolytic deposition technique, a coating technique, or a firing technique. A process of forming the metal oxide semiconductor layer 12 using an electrolytic deposition technique may include providing an electrolytic bath liquid containing fine particles of a metal oxide semiconductor material and depositing the fine particles on the conductive layer 11B of the conductive substrate 11 in the electrolytic bath liquid so that the metal oxide semiconductor material is precipitated thereon. A process of forming the metal oxide semiconductor layer 12 using a coating technique may include applying, to the conductive substrate 11, a dispersion (metal oxide slurry) containing dispersed fine particles of a metal oxide semiconductor material and then drying the applied dispersion to remove the dispersion medium from the dispersion. A process of forming the metal oxide semiconductor layer 12 using a firing technique may include applying a metal oxide slurry to the conductive substrate 11 in the same way as in the coating technique, drying the slurry, and then firing the dried material. Especially when an electrolytic deposition technique or a coating technique is used to form the metal oxide semiconductor layer 12, a less heat-resistant plastic material or polymer film material can be used as the substrate 11A, so that a highly flexible electrode can be formed.

The metal oxide semiconductor layer 12 may also be treated with an organic base, a urea derivative, or a cyclic sugar chain. Examples of the organic base include diarylamine, triarylamine, pyridine, 4-tert-butylpyridine, polyvinyl pyridine, quinoline, piperidine, and amidine. The treatment may be performed before or after the dye 13 is adsorbed as described below. The treatment method may be an immersion treatment, and a solid treatment agent may be dissolved in an organic solvent and then be used for the immersion treatment.

The dye 13, which is typically adsorbed to the metal oxide semiconductor layer 12, includes one or more dyes (sensitizing dyes) capable of injecting electrons into the metal oxide semiconductor layer 12 when excited by absorbing light. In the photoelectric conversion device of the invention, the novel compound of the invention represented by formula (1) corresponds to the dye 13. When the novel compound of the invention is used as the dye 13, the ratio of the amount of electrons injected from the whole of the dye 13 into the metal oxide semiconductor layer 12 to the amount of applied light will be higher, so that the conversion efficiency will be higher.

The dye 13 only has to include at least one novel compound of the invention represented by formula (1) and may include any other dye. Examples of any other dye include organic dyes (hereinafter referred to as other organic dyes) and organometallic complex compounds, and preferably include dyes having a group capable of adsorbing to the metal oxide semiconductor layer 12 (support).

Examples of other organic dyes include eosin Y, dibromofluorescein, fluorescein, rhodamine B, pyrogallol, dichlorofluorescein, Erythrosine B (Erythrosine is a registered trademark), fluorescin, mercurochrome, cyanine dyes, merocyanine disazo dyes, trisazo dyes, anthraquinone dyes, polycyclic quinone dyes, indigo dyes, diphenylmethane dyes, trimethylmethane dyes, quinoline dyes, benzophenone dyes, naphthoquinone dyes, perylene dyes, fluorenone dyes, squarylium dyes, azulenium dyes, perinone dyes, quinacridone dyes, metal-free phthalocyanine dyes, metal-free porphyrin dyres, or metal-free azaporphyrin dyes.

Examples of organometallic complex compounds include organometallic complex compounds having both an ionic coordinate bond, which is formed between a metal cation and a nitrogen anion in an aromatic heterocyclic ring, and a nonionic coordinate bond, which is formed between a metal cation and a nitrogen atom or a chalcogen atom; and organometallic complex compounds having both an ionic coordinate bond, which is formed between a metal cation and an oxygen anion or a sulfur anion, and a nonionic coordinate bond, which is formed between a metal cation and a nitrogen atom or a chalcogen atom. Specific examples include metal phthalocyanine dyes such as copper phthalocyanine, titanyl phthalocyanine, cobalt phthalocyanine, nickel phthalocyanine, and iron phthalocyanine; metal naphthalocyanine dyes, metal porphyrin dyes, metal azaporphyrin dyes; and bipyridyl, terpyridyl, phenanthroline, bicinchoninate, azo, or quinolinol metal complexes with ruthenium, iron, or osmium, and other ruthenium complexes.

In addition to the above dye, the dye 13 may also contain one or more additives. Examples of such additives include association inhibitors capable of inhibiting the association of compounds in the dye, such as cholic acid compounds represented by chemical formula (13). Any of such additives may be used alone or in mixture of two or more.

(13)

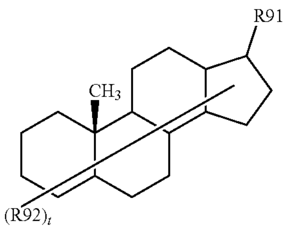

In the formula, R91 represents an alkyl group having an acidic group, R92 represents a group bonded to any of the carbon atoms of the steroid skeleton and selected from a hydroxyl group, a halogen group, an alkyl group, an alkoxy group, an aryl group, a heterocyclic group, an acyl group, an acyloxy group, an oxycarbonyl group, an oxo group, an acidic group, or a derivative of any of these groups, R92 groups may be the same or different, t represents an integer of 1 to 5, and any carbon-carbon bond in the steroid skeleton may be a single bond or a double bond.

For example, the counter electrode 20 includes a conductive substrate 21 and a conductive layer 22 provided on the substrate 21. The counter electrode 20 functions as a positive electrode for the external circuit. Examples of the material for the conductive substrate 21 may include those for the substrate 11A of the conductive substrate 11 in the working electrode 10. The conductive layer 22 includes one or more conductive materials and optionally a binder. For example, the conductive material used to form the conductive layer 22 may be a metal such as platinum, gold, silver, copper (Cu), rhodium (Rh), ruthenium (Ru), aluminum (Al), magnesium (Mg), or indium (In), carbon (C), or a conductive polymer. For example, the binder that may be used to form the conductive layer 22 may be acrylic resin, polyester resin, phenolic resin, epoxy resin, cellulose, melamine resin, fluoroelastomer, or polyimide resin. Alternatively, for example, the counter electrode 20 may be a monolayer structure of the conductive layer 22.

For example, the electrolyte-containing layer 30 includes a redox electrolyte having a redox couple. For example, the redox electrolyte may be an $I^-/I_3^-$ system, a $Br^-/Br_3^-$ system, a quinone/hydroquinone system, a Co complex system, or a nitroxy radical compound system. More specifically, the redox electrolyte may be a combination of a halide salt and elementary halogen, such as a combination of an iodide salt and elementary iodine or a combination of a bromide salt and bromine. Examples of such a halide salt include cesium halide, quaternary alkyl ammonium halides, imidazolium halides, thiazolium halides, oxazolium halides, quinolinium halides, or pyridinium halides. Specific examples of the iodide salts include cesium iodide, quaternary alkyl ammonium iodides such as tetraethyl ammonium iodide, tetrapropyl ammonium iodide, tetrabutyl ammonium iodide, tetrapentyl ammonium iodide, tetrahexyl ammonium iodide, tetraheptyl ammonium iodide, or trimethylphenyl ammonium iodide; imidazolium iodides such as 3-methylimidazolium iodide or 1-propyl-2,3-dimethylimidazolium iodide; thiazolium iodides such as 3-ethyl-2-methyl-2-thiazolium iodide, 3-ethyl-5-(2-hydroxyethyl)-4-methylthiazolium iodide, or 3-ethyl-2-methylbenzothiazolium iodide; oxazolium iodides such as 3-ethyl-2-methyl-benzoxazolium iodide; quinolinium iodides such as 1-ethyl-2-methylquinolinium iodide; and pyridinium iodides. Examples of the bromide salts include quaternary alkyl ammonium bromide. The combination of a halide salt and elementary halogen is preferably a combination of at least one of the above iodide salts and elementary iodine.

Alternatively, for example, the redox electrolyte may a combination of an ionic liquid and elementary halogen. In this case, the redox electrolyte may further contain the halide salt or the like. Examples of the ionic liquid include those capable of being used in batteries or solar cells, such as those disclosed in publications such as Inorg. Chem. (1996), 35, pp. 1168-1178, Electrochemistry (2002), 2, pp. 130-136, Japanese Patent Application National Publication (Laid-Open) No. 09-507334, or JP-A No. 08-259543. In particular, the ionic liquid is preferably a salt having a melting point lower than room temperature (25° C.) or a salt that can be liquefied at room temperature when dissolved with any other molten salt or the like although it has a melting point higher than room temperature. Examples of the ionic liquid include the anions and the cations shown below.

Examples of ionic liquid cations include ammonium, imidazolium, oxazolium, thiazolium, oxadiazolium, triazolium, pyrrolidinium, pyridinium, piperidinium, pyrazolium, pyrimidinium, pyrazinium, triazinium, phosphonium, sulfonium, carbazolium, indolium, or a derivative of any of the above. Any of these cations may be used alone or in mixture of two or more. Specific examples include 1-methyl-3-propylimidazolium, 1-butyl-3-methylimidazolium, 1,2-dimethyl-3-propylimidazolium, and 1-ethyl-3-methylimidazolium.

Examples of ionic liquid anions include metal chlorides such as $AlCl_4^-$ and $Al_2Cl_7^-$, fluorine-containing ions such as $PF_6^-$, $BF_4^-$, $CF_3SO_3^-$, $N(CF_3SO_2)_2^-$, $F(HF)_n^-$, and $CF_3COO^-$, fluorine-free compound ions such as $NO_3^-$, $CH_3COO^-$, $C_6H_{11}COO^-$, $CH_3OSO_3^-$, $CH_3OSO_2^-$, $CH_3SO_3^-$, $CH_3SO_2^-$, $(CH_3O)_2PO_2^-$, $N(CN)_2^-$, and $SCN^-$, and halide ions such as iodide ions, and bromide ions. Any of these ions may be used alone or in mixture of two or more. In particular, the ionic liquid anion is preferably an iodide ion.

The electrolyte-containing layer 30 may be produced using a liquid electrolyte (electrolytic solution), which is a solution of the redox electrolyte in a solvent, or using a solid polymer electrolyte including an electrolytic solution contained in a polymer material. Alternatively, the electrolyte-containing layer 30 may be produced using a solidified (paste-like) electrolyte including a mixture of an electrolytic solution and a particulate carbon material such as carbon black. The carbon material-containing solidified electrolyte does not need to contain elementary halogen because the carbon material has the function of catalyzing the redox reaction. Such a redox electrolyte may contain one or more organic solvents in which the halide salt, the ionic liquid, or the like is soluble. Such an organic solvent may be an electrochemically inert organic solvent, such as acetonitrile, propionitrile, butyronitrile, methoxyacetonitrile, 3-methoxypropionitrile, valeronitrile, dimethyl carbonate, ethyl methyl carbonate, ethylene carbonate, propylene carbonate, N-methylpyrrolidone, pentanol, quinoline, N,N-dimethylformamide, γ-butyrolactone, dimethyl sulfoxide, or 1,4-dioxane.

For an improvement in the generating efficiency or durability of the photoelectric conversion device or other purposes, the electrolyte-containing layer 30 may also contain an additive such as an acyclic sugar (JP-A No. 2005-093313), a pyridine compound (JP-A No. 2003-331936), a urea derivative (JP-A No. 2003-168493), or a gelling agent (dibenzylidine-D-sorbitol, a cholesterol derivative, an amino acid derivative, an alkylamide derivative of trans-(1R,2R)-1,2-cyclohexanediamine, an alkyl urea derivative, N-octyl-D-gluconamide benzoate, an amphiphilic amino acid derivative, a quaternary ammonium derivative, the layered clay mineral disclosed in Japanese Patent No. 4692694, or a photo-polymerizable monomer such as an acrylic acid monomer).

When the dye 13 supported on the working electrode 10 in the photoelectric conversion device is irradiated with light (sunlight, or ultraviolet light, visible light, or near infrared light equivalent to sunlight), the dye 13 is excited by absorbing the light to inject electrons into the metal oxide semiconductor layer 12. The electrons are transferred to the adjacent conductive layer 11B and then reach the counter electrode 20 via the external circuit. On the other hand, in the electrolyte-containing layer 30, the electrolyte is oxidized so that the dye 13, which is oxidized with the electron transfer, can return (or be reduced) to its ground state. This oxidized electrolyte receives the above electrons. Thus, the electrons transfer between the working electrode 10 and the counter electrode 20 and the associated redox reaction in the electrolyte-containing layer 30 are repeated. This generates continuous transfer of electrons to enable steady photoelectric conversion.

For example, the photoelectric conversion device of the invention can be fabricated as described below.

The working electrode 10 is first formed. The metal oxide semiconductor layer 12 having a porous structure is first formed on the conductive layer 11B-side surface of the conductive substrate 11 using an electrolytic deposition technique or a firing technique. When the metal oxide semiconductor layer 12 is formed using an electrolytic deposition technique, for example, an electrolyte bath containing a metal salt for forming a metal oxide semiconductor material is set to a predetermined temperature while the electrolyte bath is bubbled with oxygen or air, and the conductive substrate 11 is immersed in the electrolyte bath when a constant voltage is applied between the conductive substrate 11 and a counter electrode. In this process, the metal oxide semiconductor material is deposited on the conductive layer 11B so as to form a porous structure. In this process, the counter electrode may be shifted as needed in the electrolyte bath. When the metal oxide semiconductor layer 12 is formed using a firing technique, for example, a metal oxide slurry, which is prepared by dispersing a powder of a metal oxide semiconductor material in a dispersion medium, is applied to the conductive substrate 11, dried, and then fired to form a porous structure. Subsequently, the dye 13 including the novel compound of the invention represented by formula (1) is dissolved in an organic solvent to form a dye solution. The conductive substrate 11 with the metal oxide semiconductor layer 12 formed thereon is immersed in the dye solution so that the dye 13 is deposited (supported) on the metal oxide semiconductor layer 12.

The concentration of the novel compound of the invention in the dye solution is preferably from $1.0\times10^{-5}$ to $1.0\times10^{-3}$ mol/dm$^3$, more preferably $5.0\times10^{-5}$ to $5.0\times10^{-4}$ mol/dm$^3$. The solvent used to form the dye solution may be of any type capable of dissolving the novel compound of the invention, examples of which include hydrocarbons such as toluene, benzene, and xylene; alcohols such as methanol, ethanol, and tert-butanol; ether alcohols such as methyl cellosolve, ethyl cellosolve, butyl cellosolve, and butyl diglycol; ketones such as acetone, methyl ethyl ketone, methyl isobutyl ketone, cyclohexanone, and diacetone alcohol; esters such as ethyl acetate, butyl acetate, and methoxyethyl acetate; acrylic esters such as ethyl acrylate and butyl acrylate; fluorinated alcohols such as 2,2,3,3,-tetrafluoropropanol; chlorinated hydrocarbons such as methylene dichloride, dichloroethane, and chloroform; and acetonitrile. Any of these organic solvents may be mixed together as desired. Toluene and acetonitrile are preferred.

Subsequently, the conductive layer 22 is formed on one side of the conductive substrate 21 to form the counter electrode 20. For example, the conductive layer 22 is formed by sputtering of a conductive material.

Finally, the dye 13-carrying surface of the working electrode 10 and the conductive layer 22-side surface of the counter electrode 20 are opposed to each other with a predetermined distance kept therebetween, and are fixed with a spacer (not shown) such as a sealant. And then, the whole is sealed, for example, except for the inlet for the electrolyte. Subsequently, the electrolyte is injected between the working electrode 10 and the counter electrode 20, and then the inlet is sealed, so that the electrolyte-containing layer 30 is formed. Thus, the photoelectric conversion device shown in FIGS. 1 and 2 is completed.

In the photoelectric conversion device of the invention, the dye 13 includes the compound of the invention represented by formula (1), and thus the dye 13 is prevented from leaching into the electrolyte-containing layer 30 from the support material (metal oxide semiconductor layer 12) carrying the dye 13, in contrast to cases where compounds other than the compound of the invention are used. Thus, the amount of the dye 13 supported on the metal oxide semiconductor layer 12 will not decrease, so that the amount of electrons injected from the dye 13 into the metal oxide semiconductor layer 12 will not decrease. Because of such an effect, the photoelectric conversion device of the invention can have higher durability.

Although the photoelectric conversion device described above has the electrolyte-containing layer 30 between the working electrode 10 and the counter electrode 20, the electrolyte-containing layer 30 may be replaced by a solid charge-transfer layer. In this case, for example, the solid charge-transfer layer has a solid material in which carrier transport takes part in electrical conduction. Such a material is preferably an electron transport material, a hole transport material, or the like.

The hole transport material is preferably an aromatic amine or a triphenylene derivative. Examples of the hole transport material include organic conductive polymers such as oligothiophene compounds, polypyrrole, polyacetylene or derivatives thereof, poly(p-phenylene) or derivatives thereof, poly(p-phenylenevinylene) or derivatives thereof, polythienylene vinylene or derivatives thereof, polythiophene or derivatives thereof, polyaniline or derivatives thereof, and polytoluidine or derivatives thereof.

Alternatively, for example, a p-type inorganic compound semiconductor may be used as the hole transport material. The p-type inorganic compound semiconductor is preferably has a band gap of 2 eV or more, more preferably 2.5 eV or more. The p-type inorganic compound semiconductor must have an ionization potential smaller than that of the working electrode 10 to create conditions under which the holes from the dye can be reduced. Although the preferred range of the ionization potential of the p-type inorganic compound semiconductor varies with the dye used, the ionization potential is preferably in the range of 4.5 eV to 5.5 eV, more preferably in the range of 4.7 eV to 5.3 eV.

For example, the p-type inorganic compound semiconductor may be a monovalent copper compound semiconductor. Examples of the monovalent copper compound semiconductor include CuI, CuSCN, $CuInSe_2$, Cu(In,Ga)$Se_2$, $CuGaSe_2$, $Cu_2O$, CuS, $CuGaS_2$, $CuInS_2$, $CuAlSe_2$, etc. Other examples of the p-type inorganic compound semiconductor include GaP, NiO, CoO, FeO, $Bi_2O_3$, $MoO_2$, $Cr_2O_3$, etc.

For example, such a solid charge-transfer layer may be formed by a method of forming a solid charge-transfer layer directly on the working electrode 10, which may be followed by forming the counter electrode 20.

For example, the hole transport material including an organic conductive polymer can be introduced into the interior of the electrode by a technique such as vacuum deposition, casting, coating, spin coating, immersion, electrolytic polymerization, or photo-electrolytic polymerization. The solid inorganic compound can also be introduced into the interior of the electrode by a technique such as casting, coating, spin coating, immersion, or electroplating. Part of the solid charge-transfer layer formed as described above (especially having a hole transport material) is preferably infiltrated into part of the pores of the porous structure of the metal oxide semiconductor layer 12 so that it can be in direct contact.

As in the case that the electrolyte-containing layer 30 is provided, the compound of the invention can also increase the conversion efficiency of the photoelectric conversion device having the solid charge-transfer layer in place of the electrolyte-containing layer 30.

The photoelectric conversion device of the invention may be used not only in solar cell applications as described above but also in other applications. For example, other applications include optical sensors, etc.

EXAMPLES

Hereinafter, the invention is more specifically described with reference to synthesis examples, examples, and comparative examples, which however are not intended to limit the invention.

The synthesis examples below show the synthesis of compound Nos. 1 to 25 and 66 to 68 listed above. Halides as precursors and silylating agents (corresponding to chemical formulae (11) and (12) above, respectively) were purchased or synthesized by known methods.

(Synthesis Example 1) Synthesis of Compound No. 1

Mixed were 4-(4-bromophenylazo)-N,N-dimethylaniline (halide, 2.0 mmol, 0.60 g), triethoxysilane (silylating agent, 3.0 mmol, 0.49 g), tris(dibenzylidineacetone)dipalladium (0.03 mmol, 0.027 (2-biphenyl)di-tert-butylphosphine (0.12 mmol, 0.036 g), N,N-diisopropylethylamine (6.0 mmol, 0.78 g), and dimethylformamide (4 ml), and stirred at 60° C. for 3 hours. After the reaction solution was cooled to room temperature, chloroform (10 ml) and water (10 ml) were added to the reaction solution, and oil-water separation was performed. The resultant organic layer was purified using PLC (with a eluent of hexane:ethyl acetate=15:1) to yield 0.35 g of a yellow solid (yield 45.2%). The resultant solid was identified as compound No. 1 using UV-VIS (λmax) and $^{1}$H-NMR. The data are shown in Tables 1 and 2.

(Synthesis Examples 2 to 28) Synthesis of Compound Nos. 2 to 25 and 66 to 68

Compound Nos. 2 to 25 and 66 to 68 were synthesized using the same method as in Synthesis Example 1, except that halides (bromides) and silylating agents suitable for the desired compounds were used instead. The appearance and yield of each resultant solid or liquid are shown in Table 1. The eluent used in the PLC purification depends on the compound and therefore is also shown in Table 1. The synthesized compounds were each identified as the desired compound in the same way as in Synthesis Example 1. The data are shown in Tables 1 and 2.

TABLE 1

| | Compound | Eluent | Appearance | Yield (%) | λmax (nm) |
|---|---|---|---|---|---|
| Synthesis Example 1 | No. 1 | HEX:AcOEt = 15:1 | Yellow solid | 45 | 421(MeOH) |
| Synthesis Example 2 | No. 2 | HEX:AcOEt = 20:1 | Yellow solid | 11 | 421(MeOH) |
| Synthesis Example 3 | No. 3 | HEX:AcOEt = 10:1 | Yellow solid | 21 | 444(MeOH) |
| Synthesis Example 4 | No. 4 | HEX:AcOEt = 20:1 | Yellow solid | 15 | 416(MeOH) |
| Synthesis Example 5 | No. 5 | HEX:AcOEt = 20:1 | Yellow solid | 6 | 415(MeOH) |
| Synthesis Example 6 | No. 6 | HEX:AcOEt = 10:1 | Yellow solid | 19 | 418(MeOH) |
| Synthesis Example 7 | No. 7 | HEX:AcOEt = 1:1 | Orange solid | 26 | 448(MeOH) |
| Synthesis Example 8 | No. 8 | HEX:AcOEt = 10:1 | Orange solid | 30 | 456(MeOH) |
| Synthesis Example 9 | No. 9 | HEX:$CHCl_3$ = 1:1 | Orange oil | 10 | 443($CHCl_3$) |
| Synthesis Example 10 | No. 10 | $CHCl_3$ | Orange solid | 28 | 461(MeOH) |
| Synthesis Example 11 | No. 11 | $CHCl_3$ | Orange solid | 57 | 452(MeOH) |
| Synthesis Example 12 | No. 12 | $CHCl_3$ | Orange solid | 25 | 474(MeOH) |
| Synthesis Example 13 | No. 13 | HEX:AcOEt = 5:1 | Yellow solid | 11 | 428($CHCl_3$) |
| Synthesis Example 14 | No. 14 | HEX:AcOEt = 5:1 | Orange solid | 41 | 455($CHCl_3$) |
| Synthesis Example 15 | No. 15 | $CHCl_3$ | Orange solid | 34 | 486($CHCl_3$) |
| Synthesis Example 16 | No. 16 | $CHCl_3$ | Orange solid | 30 | 482($CHCl_3$) |
| Synthesis Example 17 | No. 17 | HEX:AcOEt = 1:1 | Orange solid | 15 | 476(MeOH) |
| Synthesis Example 18 | No. 18 | HEX:AcOEt = 10:1 | Orange solid | 11 | 453(MeOH) |
| Synthesis Example 19 | No. 19 | HEX:AcOEt = 10:1 | Orange solid | 1 | 453($CHCl_3$) |
| Synthesis Example 20 | No. 20 | HEX:AcOEt = 10:1 | Orange solid | 16 | 448($CHCl_3$) |
| Synthesis Example 21 | No. 21 | $CHCl_3$ | Orange solid | 2 | 490($CHCl_3$) |

TABLE 1-continued

| | Compound | Eluent | Appearance | Yield (%) | λmax (nm) |
|---|---|---|---|---|---|
| Synthesis Example 22 | No. 22 | HEX:AcOEt = 20:1 | Yellow oil | 21 | 407($CHCl_3$) |
| Synthesis Example 23 | No. 23 | HEX:AcOEt = 20:1 | Yellow oil | 35 | 366($CHCl_3$) |
| Synthesis Example 24 | No. 24 | HEX:AcOEt = 20:1 | Yellow oil | 26 | 407($CHCl_3$) |
| Synthesis Example 25 | No. 25 | HEX:AcOEt = 10:1 | Yellow solid | 36 | 385($CHCl_3$) |
| Synthesis Example 26 | No. 66 | HEX:AcOEt = 3:1 | Yellow oil | 14 | 411($CHCl_3$) |
| Synthesis Example 27 | No. 67 | $CHCl_3$ | Orange solid | 11 | 463($CHCl_3$) |
| Synthesis Example 28 | No. 68 | $CHCl_3$ | Orange solid | 14 | 467($CHCl_3$) |

HEX: hexane
AcOEt: ethyl acetate

TABLE 2-1

<$^1$H-NMR; $CDCl_3$>

| | Compound | δ/ppm (proton number, multiplicity) |
|---|---|---|
| Synthesis Example 1 | No. 1 | 7.90 (d, 2H), 7.84-7.78 (m, 4H), 6.77 (d, 2H), 3.90 (q, 4H), 3.11 (s, 6H), 1.27 (t, 6H) |
| Synthesis Example 2 | No. 2 | 7.89 (d, 2H), 7.83-7.77 (m, 4H), 7.69 (d, 2H), 7.44-7.37 (m, 3H), 6.76 (d, 2H), 3.90 (q, 4H), 3.10 (s, 6H), 1.28 (t, 6H) |
| Synthesis Example 3 | No. 3 | 7.87 (d, 2H), 7.83 (d, 2H), 7.36 (d, 1H), 7.32 (d, 1H), 7.17 (d, 1H), 7.04 (d, 1H), 6.76 (d, 2H), 3.91 (q, 6H), 3.10 (s, 6H), 1.28 (t, 9H) |
| Synthesis Example 4 | No. 4 | 7.88 (d, 2H), 7.81 (d, 2H), 7.74 (d, 2H), 6.75 (d, 2H), 3.83 (q, 4H), 3.09 (s, 6H), 1.24 (t, 6H), 0.39 (s, 3H) |
| Synthesis Example 5 | No. 5 | 7.88 (d, 2H), 7.80 (d, 2H), 7.68 (d, 2H), 6.73 (d, 2H), 3.68 (q, 2H), 3.07 (s, 6H), 1.19 (t, 3H), 0.42 (s, 3H), 0.41 (s, 3H) |
| Synthesis Example 6 | No. 6 | 7.88 (d, 2H), 7.83 (d, 2H), 7.75 (d, 2H), 6.75 (d, 2H), 3.64 (s, 9H), 3.09 (s, 6H) |
| Synthesis Example 7 | No. 7 | 8.64 (s, 1H), 8.15 (s, 1H), 7.67 (d, 1H), 7.62 (d, 1H), 6.66 (d, 1H), 6.56 (d, 1H), 3.92 (q, 6H), 3.48 (q, 4H), 1.29-1.20 (m, 15H) |
| Synthesis Example 8 | No. 8 | 7.89 (s, 1H), 7.66 (d, 1H), 7.60-6.89 (m, 8H), 6.63 (d, 1H), 6.55 (d, 1H), 3.89 (q, 6H), 3.38 (q, 4H), 1.27 (t, 9H), 1.04 (t, 6H) |
| Synthesis Example 9 | No. 9 | 8.61 (s, 1H), 7.35 (m, 8H), 6.59 (d, 1H), 6.54 (s, 1H), 3.92 (q, 6H), 3.46 (q, 4H), 1.24 (m, 15H) |
| Synthesis Example 10 | No. 10 | 7.87 (s, 1H), 7.75 (d, 1H), 7.65-7.56 (m, 2H), 7.44-7.31 (m, 3H), 7.12 (d, 2H), 7.02 (d, 1H), 6.60 (d, 1H), 6.51 (d, 1H), 3.92 (q, 6H), 3.35 (t, 4H), 1.63 (quin, 4H), 1.40 (sext, 4H), 1.28 (t, 9H), 1.00 (t, 6H) |
| Synthesis Example 11 | No. 11 | 7.86 (s, 1H), 7.54 (d, 1H), 7.31 (d, 1H), 7.18-7.11 (m, 2H), 6.61 (dd, 1H), 6.53 (d, 1H), 3.89 (q, 6H), 3.43 (q, 4H), 2.71 (t, 2H), 1.63 (quin, 2H), 1.33-1.23 (m, 21H), 0.90 (t, 3H) |
| Synthesis Example 12 | No. 12 | 7.87 (s, 1H), 7.54 (d, 1H), 7.33 (d, 1H), 7.32 (d, 1H), 7.14-7.08 (m, 4H), 7.00 (d, 1H), 6.62 (dd, 1H), 6.54 (d, 1H), 3.91 (q, 6H), 3.44 (q, 4H), 2.64 (t, 2H), 1.63 (quin, 2H), 1.35-1.21 (m, 21H), 0.91 (t, 2H) |
| Synthesis Example 13 | No. 13 | 7.89 (s, 1H), 7.66 (d, 1H), 7.31-7.34 (m, 2H), 7.09 (dd, 1H), 6.51 (s, 1H), 3.92 (q, 6H), 3.34 (t, 4H), 1.58-1.66 (m, 4H), 1.35-1.42 (m, 4H), 1.28 (t, 9H), 0.98 (t, 6H) |
| Synthesis Example 14 | No. 14 | 7.84 (s, 1H), 7.54 (d, 1H), 7.30-7.26 (m, 2H), 6.90 (d, 1H), 6.78 (d, 1H), 6.58 (dd, 1H), 6.50 (s, 1H), 4.47-4.13 (m, 8H), 3.92 (q, 6H), 3.34 (t, 4H), 1.61 (quin, 4H), 1.38 (sext, 4H), 1.32-1.24 (m, 13H), 0.98 (t, 6H) |

TABLE 2-1-continued

| <$^1$H-NMR; $CDCl_3$> | | |
|---|---|---|
| | Compound | δ/ppm (proton number, multiplicity) |
| Synthesis Example 15 | No. 15 | 7.79 (s, 1H), 7.52 (d, 1H), 7.33 (d, 1H), 7.13-7.09 (m, 4H), 6.99 (s, 1H), 6.91 (s, 1H), 3.91 (q, 6H), 3.29 (q, 4H), 2.93 (t, 2H), 2.79 (t, 2H), 2.64 (t, 2H), 1.98 (sext, 4H), 1.63 (t, 2H), 1.40-1.24 (m, 13H), 0.90 (t, 3H) |

TABLE 2-2

| <$^1$H-NMR; $CDCl_3$> | | |
|---|---|---|
| | Compound | δ/ppm (proton number, multiplicity) |
| Synthesis Example 16 | No. 16 | 7.79 (s, 1H), 7.52 (d, 1H), 7.41 (d, 1H), 7.33 (d, 1H), 7.13-7.01 (m, 4H), 6.90 (d, 2H), 3.91 (q, 6H), 3.29 (q, 4H), 2.92 (t, 2H), 2.78 (t, 4H), 2.66 (t, 2H), 1.99 (sext, 4H), 1.72-1.61 (m, 4H), 1.42-1.21 (m, 21H), 0.91 (t, 6H) |
| Synthesis Example 17 | No. 17 | 7.74-7.70 (m, 4H), 7.43 (s, 1H), 7.27 (s, 1H), 6.95 (s, 1H), 6.64 (dd, 1H), 6.37 (d, 1H), 3.90 (q, 6H), 3.43 (q, 4H), 1.29-1.22 (m, 15H) |
| Synthesis Example 18 | No. 18 | 7.64 (d, 2H), 7.56 (d, 2H), 7.51 (s, 1H), 7.40 (d, 1H), 6.97 (d, 1H), 3.89 (q, 6H), 3.35 (t, 4H), 1.66 (quin, 4H), 1.39 (sext, 4H), 1.26 (t, 9H), 0.98 (t, 6H) |
| Synthesis Example 19 | No. 19 | 8.40 (d, 1H), 8.16 (d, 1H), 7.86 (d, 1H), 7.47-7.34 (m, 8H), 7.27-6.90 (m, 19H), 3.98 (q, 6H), 1.61 (s, 12H), 1.33 (t, 9H) |
| Synthesis Example 20 | No. 20 | 8.16 (t, 2H), 8.06 (t, 2H), 7.43-7.37 (m, 5H), 7.25-7.10 (m, 11H), 7.01-6.92 (m, 8H), 6.68 (d, 1H), 4.50-4.19 (m, 8H), 3.90 (q, 6H), 2.76 (t, 2H), 1.71 (quin, 2H), 1.61 (s, 12H), 1.45-1.23 (m, 15H), 0.91 (t, 3H) |
| Synthesis Example 21 | No. 21 | 8.24 (m, 5H), 7.85 (d, 1H), 7.55 (d, 1H), 7.51-7.37 (m, 11H), 7.27-7.17 (m, 8H), 3.97 (q, 6H), 2.85 (t, 2H), 2.63 (t, 4H), 1.72-1.65 (m, 6H), 1.44-1.27 (m, 23H), 0.94-0.89 (m, 9H) |
| Synthesis Example 22 | No. 22 | 8.30 (s, 1H), 8.13 (d, 1H), 7.71 (dd, 1H), 7.46 (dd, 1H), 7.40 (dd, 2H), 7.34 (d, 1H), 7.25 (dd, 2H), 7.12 (dd, 2H), 7.04 (d, 1H), 4.37 (q, 2H), 3.91 (q, 6H), 2.71 (t, 2H), 1.66-1.70 (m, 2H), 1.20-1.47 (m, 18H), 0.91 (t, 3H) |
| Synthesis Example 23 | No. 23 | 8.34 (d, 1H), 8.14 (d, 1H), 7.78 (s, 1H), 7.73 (dd, 1H), 7.58 (d, 1H), 7.55 (d, 1H), 7.48 (d, 1H), 7.39-7.43 (m, 3H), 7.28-7.32 (m, 2H), 7.15 (s, 1H), 6.93 (d, 1H), 4.39 (q, 2H), 3.92 (q, 6H), 2.74 (t, 2H), 1.66-1.76 (m, 2H), 1.16-1.48 (m, 18H), 0.91 (t, 3H) |
| Synthesis Example 24 | No. 24 | 7.45-7.33 (m, 3H), 7.14-6.97 (m, 14H), 6.65 (d, 1H), 6.58 (d, 1H), 3.91 (q, 6H), 2.65 (t, 2H), 1.62 (quin, 2H), 1.33-1.16 (m, 15H), 0.90 (t, 3H) |
| Synthesis Example 25 | No. 25 | 7.31-7.34 (m, 3H), 7.24-7.28 (m, 4H), 7.09-7.15 (m, 6H), 7.01-7.05 (m, 4H), 3.90 (q, 6H), 1.26 (t, 9H) |
| Synthesis Example 26 | No. 66 | 7.45 (d, 1H), 7.33 (d, 1H), 7.13 (d, 1H), 7.11 (s, 1H), 6.99 (d, 1H), 6.92 (s, 1H), 6.88 (s, 1H), 6.60 (dd, 1H), 6.50 (d, 1H), 3.91 (q, 6H), 3.42 (q, 4H), 2.81 (m, 2H), 2.65(m, 2H), 2.44 (s, 3H), 1.67 (m, 4H), 1.35 (m, 17H), 1.20 (m, 6H), 0.90(t, 6H) |
| Synthesis Example 27 | No. 67 | 7.89 (s, 1H), 7.74 (d, 1H), 7.63-7.55 (m, 3H), 7.42-7.14 (m, 4H), 7.09 (d, 1H), 6.62 (d, 1H), 6.54 (s, 1H), 3.91 (q, 6H), 3.44 (q, 4H), 1.29-1.22 (m, 15H) |
| Synthesis Example 28 | No. 68 | 7.87 (s, 1H), 7.56 (d, 1H), 7.34-7.31 (m, 2H), 7.11 (d, 3H), 7.01 (d, 1H), 6.61 (dd, 1H), 6.53 (d, 1H) |

Support materials according to the invention were prepared by the procedure described below using the compounds synthesized as described above.

(Example 1) Support Material (Working Electrode) Produced with Compound No. 1

First prepared was the conductive substrate 11 made of a 2.0 cm long, 1.5 cm wide, 1.1 mm thick conductive glass substrate (F—$SnO_2$). Subsequently, 70 μm thick masking tapes were bonded to the conductive substrate 11 so as to surround a 0.5 cm long, 0.5 cm wide square area, and 3 $cm^3$ of a metal oxide slurry was applied in uniform thickness to the square area and then dried. The metal oxide slurry used was a suspension of 10% by weight of titanium oxide powder ($TiO_2$, Ti-Nanoxide D manufactured by Solaronix SA.) in water. Subsequently, the masking tapes were peeled off from the conductive substrate 11, and the substrate was fired at 450° C. in an electric furnace, so that the metal oxide semiconductor layer 12 with a thickness of about 5 μm was formed. Subsequently, compound No. 1 was dissolved at a concentration of $3\times10^{-4}$ mol/$dm^3$ in toluene to form a dye solution. The conductive substrate 11 with the metal oxide semiconductor layer 12 formed thereon was immersed in the dye solution, so that the dye 13-carrying working electrode 10 was formed.

The formed working electrode 10 was immersed in a remover (acetonitrile:water=99:1) under the conditions of 25° C. and 24 hours. Table 3 shows the amount of the supported dye (the absorbance (Abs.) of the dye at λmax) after the immersion in the remover, as a measure of the resistance to removal, when the amount of the supported dye before the immersion in the remover is normalized as 100. It can be concluded that the closer to 100 the amount of the supported dye after the removal is, the higher the resistance to removal.

Examples 2 to 22 and Comparative Examples 1 to 5

The working electrode 10 carrying each dye was prepared using the same process as in Example 1, except that the metal slurry shown in Table 3 was used and that compound No. 1 was replaced by the compound shown in Table 3, and the resistance of the dye to removal was determined as in Example 1. The results are shown in Table 3. Zinc oxide powder (FINEX-50 manufactured by Sakai Chemical Industry Co., Ltd., 20 nm in average particle size) was used as ZnO for the metal slurry shown in Table 3.

TABLE 3

| | Metal slurry | Compound | Resistance to removal |
|---|---|---|---|
| Example 1 | $TiO_2$ | No. 1 | 66 |
| Example 2 | $TiO_2$ | No. 7 | 90 |
| Example 3 | $TiO_2$ | No. 8 | 59 |
| Example 4 | $TiO_2$ | No. 10 | 75 |
| Example 5 | $TiO_2$ | No. 12 | 91 |
| Example 6 | $TiO_2$ | No. 13 | 75 |
| Example 7 | $TiO_2$ | No. 14 | 80 |
| Example 8 | $TiO_2$ | No. 15 | 99 |
| Example 9 | $TiO_2$ | No. 17 | 50 |
| Example 10 | $TiO_2$ | No. 18 | 66 |
| Example 11 | $TiO_2$ | No. 22 | 88 |
| Example 12 | $TiO_2$ | No. 24 | 77 |
| Example 13 | $TiO_2$ | No. 25 | 66 |
| Example 14 | ZnO | No. 6 | 72 |
| Example 15 | ZnO | No. 7 | 100 |

TABLE 3-continued

| | Metal slurry | Compound | Resistance to removal |
|---|---|---|---|
| Example 16 | ZnO | No. 8 | 68 |
| Example 17 | ZnO | No. 10 | 69 |
| Example 18 | ZnO | No. 12 | 100 |
| Example 19 | ZnO | No. 15 | 100 |
| Example 20 | ZnO | No. 18 | 84 |
| Example 21 | ZnO | No. 22 | 90 |
| Example 22 | ZnO | No. 24 | 69 |
| Comparative Example 1 | $TiO_2$ | Comparative 1 | 19 |
| Comparative Example 2 | $TiO_2$ | Comparative 2 | 18 |
| Comparative Example 3 | $TiO_2$ | Comparative 3 | 39 |
| Comparative Example 4 | $TiO_2$ | Comparative 4 | 0 |
| Comparative Example 5 | ZnO | Comparative 3 | 26 |

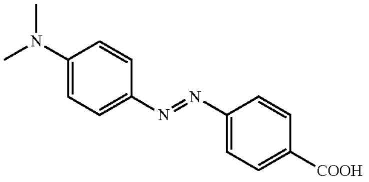

Comparative 1

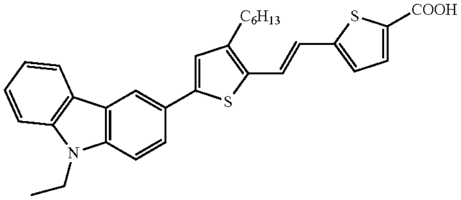

Comparative 2

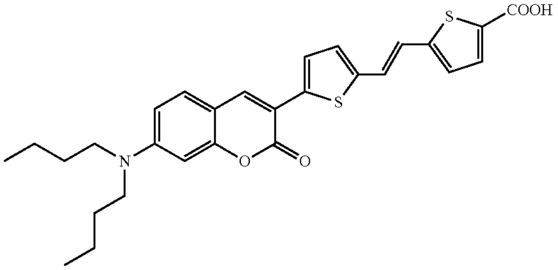

Comparative 3

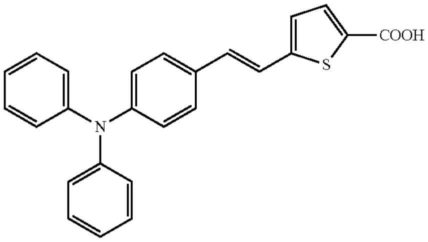

Comparative 4

The results of the resistance to removal in Table 3 (especially, comparisons of Example 1 and Comparative Example 1, Example 11 and Comparative Example 2, Example 4 and Comparative Example 3, Example 13 and Comparative Example 4, and Example 17 and Comparative Example 5) show that the compound of the invention represented by formula (1) has high adsorption durability. This shows that photoelectric conversion devices produced using the compound of the invention can stably and continuously maintain its photoelectric conversion efficiency.

The invention claimed is:

1. A novel compound represented by formula (1):

(1)

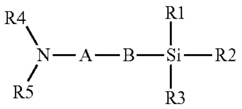

wherein

A represents an optionally substituted aromatic hydrocarbon ring group or an optionally substituted aromatic heterocyclic group, B represents a group comprising a chain of one to four pieces of one or more groups selected from groups represented by formulae (B-1) to (B-13) below, R1, R2, and R3 each represent an optionally substituted hydrocarbon group or an optionally substituted hydrocarbonoxy group, at least one of R1, R2, and R3 represents an optionally substituted hydrocarbonoxy group, R4 and R5 each represent an optionally substituted hydrocarbon group, R4 and R5 may be linked together to form a ring, and R4 and R5 may be each independently linked with A to form a ring, (B-1)

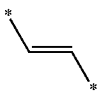

(B-2)

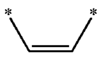

(B-3)

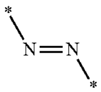

(B-4)

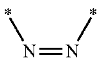

(B-5)

(B-6)

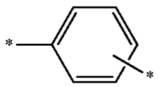

(B-7)

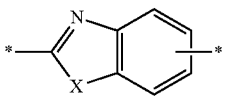

(B-8)

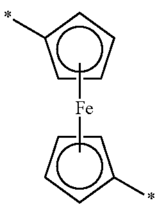

-continued (B-9)

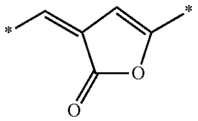

(B-10)

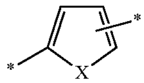

(B-11)

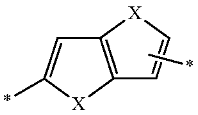

(B-12)

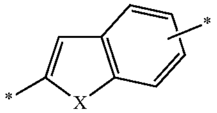

(B-13)

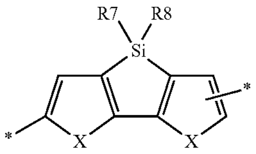

wherein

X represents S, O, or NR, wherein R represents an optionally substituted hydrocarbon group, and any hydrogen atom may be replaced by a fluorine atom, a chlorine atom, a bromine atom, an iodine atom, a cyano group, a nitro group, a hydroxyl group, a thiol group, an —NR7R8 group, or an optionally substituted aliphatic hydrocarbon group, wherein R7 and R8 each represent an optionally substituted hydrocarbon group, wherein partial structure (3) shown below in formula (1) is partial structure (3-1) or (3-2) shown below, (3)

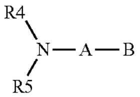

wherein A, B, R4, and R5 have the same meanings as in formula (1), (3-1)

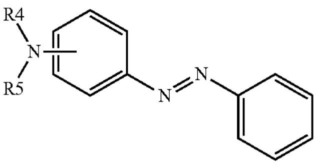

(3-2)

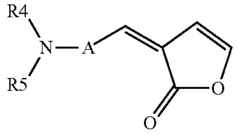

wherein A, R4, and R5 have the same meanings as in formula (1).

2. The novel compound according to claim 1, which satisfies at least one of the following conditions (i) to (iii):

(i) the group represented by B has at least one piece of group represented by any one of formulae (B-1) to (B-9) and (B-11) to (B-13);

(ii) R4 and R5 each represent an optionally substituted hydrocarbon group of 1 to 12 carbon atoms; and (iii) at least one of R4 and R5 is linked with A to form a ring, and wherein partial structure (3) shown below in formula (1) is partial structure (3-1) or (3-2) shown below,

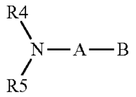

(3)

wherein A, B, R4, and R5 have the same meanings as in formula (1),

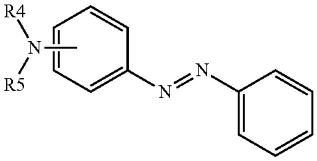

(3-1)

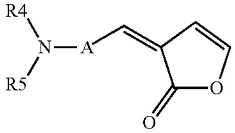

(3-2)

wherein A, R4, and R5 have the same meanings as in formula (1).

3. The novel compound according to claim 1, wherein R1, R2, and R3 in formula (1) each represent a linear or branched aliphatic hydrocarbonoxy group, and wherein partial structure (3) shown below in formula (1) is partial structure (3-1) or (3-2) shown below,

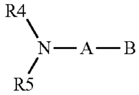

(3)

wherein A, B, R4, and R5 have the same meanings as in formula (1),

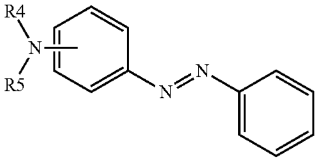

(3-1)

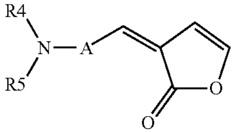

(3-2)

wherein A, R4, and R5 have the same meanings as in formula (1).

4. A support material comprising a support and the novel compound according to claim 1 supported on the support.

* * * * *